(12) United States Patent
Ueno

(10) Patent No.: US 8,202,909 B2
(45) Date of Patent: Jun. 19, 2012

(54) METHOD FOR TREATING CENTRAL NERVOUS SYSTEM DISORDERS

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 1151 days.

(21) Appl. No.: 11/339,495

(22) Filed: Jan. 26, 2006

(65) Prior Publication Data

US 2006/0194880 A1 Aug. 31, 2006

Related U.S. Application Data

(60) Provisional application No. 60/647,008, filed on Jan. 27, 2005.

(51) Int. Cl.
*A01N 37/08* (2006.01)
*A01N 53/00* (2006.01)
*A61K 31/557* (2006.01)
*C07C 59/147* (2006.01)
*C07C 59/185* (2006.01)

(52) U.S. Cl. .................. 514/573; 554/117; 554/118

(58) Field of Classification Search .............. 514/573; 554/117, 118
See application file for complete search history.

(56) References Cited

U.S. PATENT DOCUMENTS

| | | | |
|---|---|---|---|
| 4,131,738 A | 12/1978 | Smith | |
| 4,138,573 A | 2/1979 | Bundy et al. | |
| 4,138,577 A * | 2/1979 | Bundy et al. | 560/55 |
| 5,290,811 A | 3/1994 | Ueno et al. | |
| 5,317,032 A | 5/1994 | Ueno et al. | |
| 6,197,821 B1 | 3/2001 | Ueno | |
| 6,414,016 B1 | 7/2002 | Ueno | |
| 2004/0224995 A1 | 11/2004 | Simpkins et al. | |

FOREIGN PATENT DOCUMENTS

| | | |
|---|---|---|
| CN | 1522699 A | 8/2004 |
| EP | 0 444 844 A2 | 4/1991 |
| EP | 435443 A2 * | 7/1991 |
| EP | 0 690 049 A2 | 1/1996 |
| GB | 1120243 | 7/1968 |
| GB | 1 377 258 | 12/1974 |
| JP | 4-187637 A | 7/1992 |
| JP | 4-211053 A | 8/1992 |
| JP | 5-58992 A | 3/1993 |
| JP | 2001-89444 A | 4/2001 |
| SU | 845774 A3 | 7/1981 |
| WO | WO 01/05388 A2 | 1/2001 |
| WO | WO 01/70233 A2 | 9/2001 |

OTHER PUBLICATIONS

Hubner et al. "Ion channel diseases" Human Molecular genetics, 2002, vol. 11, No. 20, pp. 2435-2445.*
Stix, Gary "Alzheimer's: Forestalling the Darkness" Scientific American, Jun. 2010, pp. 51-57.*
G. Bazzoni, et al., "Endothelial Cell-to-Cell Junctions: Molecular Organization and Role in Vascular Homeostasis", Physiol. Rev., vol. 84, No. 3, pp. 869-901, Jul. 2004.
W. Risau, et al., "Development of the blood-brain barrier", Trends Neurosci. (TINS), vol. 13, No. 5, 1990, pp. 174-178.
H. E. De Vries, et al., "The Blood-Brain Barrier in Neuroinflammatory Diseases", Pharmacological Reviews, vol. 49, No. 2, pp. 143-155, 1997.
D. C. Davies, "Blood-brain barrier breakdown in septic encephalopathy and brain tumours", J. Anat., vol. 200, No. 6, pp. 639-646, 2002.
R. Härtl, et al., "Blood-Brain Barrier Breakdown Occurs Early After Traumatic Brian Injury and is not Related to White Blood Cell Adherence", Acta Neurochir (Suppl), 70, pp. 240-242, 1997.
A. M. Robert, et al., "Action of Proteolytic and Glycolytic Enzymes on the Permeability of the Blood-Brain Barrier", Biomedicine, 21, pp. 36-39, 1974.
A. M. Romanic et al.., "Matrix Metalloproteinase Expression Increases After Cerebral Focal Ischemia in Rats: Inhibition of Matrix Metalloproteinase-9 Reduces Infarct Size", Stroke, vol. 29, No. 5, pp. 1020-1030, 1998.
J. M. Wardlaw, et al., "Is Breakdown of the Blood-Brain Barrier Responsible for Lacunar Stroke, Leukoaraiosis, and Dementia?", Stroke, vol. 34, No. 3, pp. 806-812, 2003.
G. A. Rosenberg, "Matrix Metalloproteinases in Brain Injury", Journal of Neurotrauma, vol. 12, No. 5, pp. 833-842, 1995.
W. J. Koroshetz, et al., "Emerging treatments for stroke in humans", Trends Pharmacol. Sci. (TiPS), vol. 17, pp. 227-233, Jun. 1996.
B. K. Siesjö, "Mechanisms of ischemic brain damage", Critical Care Medicine, vol. 16, No. 10, pp. 954-963, 1988.
Database WPI Week 200479 Derwent Publications Ltd., London, GB; AN 2004-797147,XP002420426.
Database WPI Week 199233 Derwent Publications Ltd., London, GB; AN 1992-274001, XP002420427.
Russian Official Action; Re: No. 0710839/44RU; (21) Application No. 2007132081/04(034990); (22) Application filing date Jan. 26, 2006; [x] (86) Application No. PCT/JP2006/301704 of Jan. 26, 2006; (71) Applicants: Sukampo AG,CH.

* cited by examiner

*Primary Examiner* — Sreeni Padmanabhan
*Assistant Examiner* — Kendra D Carter
(74) *Attorney, Agent, or Firm* — Sughrue Mion, PLLC

(57) ABSTRACT

The present invention provides a method for treating a central nervous system disorder in a mammalian subject, which comprises administering an effective amount of a 11-deoxy-prostaglandin compound to a subject in need thereof. The invention also provide novel 11-deoxy-prostaglandin compound.

14 Claims, 19 Drawing Sheets

METHOD FOR TREATING CENTRAL NERVOUS SYSTEM DISORDERS

CROSS-REFERENCE TO RELATED APPLICATIONS

The Applicant claims the benefit of U.S. Provisional Application No. 60/647,008 filed Jan. 27, 2005.

TECHNICAL FIELD

The present invention relates to a method for treating a central nervous system disorder in a mammalian subject. The invention also relates to a novel prostaglandin compound.

BACKGROUND ART

Intercellular junctions mediate adhesion and communication between adjoining endothelial and epithelial cells. In the endothelium, junctional complexes comprise tight junctions, adherens junctions, and gap junctions. The expression and organization of these complexes depend on the type of vessels and the permeability requirements of perfused organs. Gap junctions are communication structures, which allow the passage of small molecular weight solutes between neighboring cells. Tight junctions serve the major functional purpose of providing a "barrier" and a "fence" within the membrane, by regulating paracellular permeability and maintaining cell polarity. Adherens junctions play an important role in contact inhibition of endothelial cell growth, paracellular permeability to circulating leukocytes and solutes. In addition, they are required for a correct organization of new vessels in angiogenesis (Physiol. Rev. 84(3), 869-901, 2004).

The mechanism by which epithelial and endothelial cells interact to form polarized tissue is of fundamental importance to multicellular organisms. Dysregulation of these barriers occurs in a variety of diseases, destroying the normal cellular environments and leading to organ failure.

Cerebral microvascular endothelial cells that form the blood-brain barrier (BBB) have tight junctions that are critical for maintaining brain homeostasis and low permeability.

The blood-brain barrier (BBB) is a specialized structure in the central nervous system (CNS), which participates in maintenance of a state of cerebrospinal fluid homeostasis by controlling the access of nutrients and toxic substances to the central nervous system (CNS).

The base membrane underlying the vasculature plays a critical role in maintaining the integrity of the BBB by providing structural support to the endothelial cell wall (Trends Neurosci. 1990; 13(5): 174-178). The BBB serves to protect the central nervous system (CNS) from invasive agents, such as inflammatory cells and bacteria, as well as from chemical agents.

A wide range of central nervous system (CNS) disorders associated with disruption of the BBB are known. Examples of the disorders include multiple sclerosis, experimental allergic encephalomyelitis, bacterial meningitis, ischemia, brain edema, Alzheimer's disease, acquired immune deficiency syndrome dementia complex (Helga E. DE Vries et al, Pharmacological Reviews, 49(2): 143-155, 1997), brain tumors (Davies D. C. et al., J Anat., 200 (6): 639-46, 2002), traumatic brain injury (Hartl R et. al., Acta Neurochir Suppl. 70: 240-242, 1997).

It has also been reported that, after focal stroke, there is a breakdown of the BBB with an associated increase in vascular permeability. Damage to the BBB often results in hemorrhage and edema, resulting in neuronal cell death (Biomedicine. 1974; 21:36-39, Stroke, 1998; 29(5): 1020-1030, Stroke, 2003; 34(3):806-812, J Neurotrauma. 1995; 12:833-842). Brain injury after focal stroke is primarily a result of the decrease in blood flow and of energy depletion due to occlusion of a cerebral blood vessel. The neuronal tissue becomes infracted as a result of these events, with contributions from excitotoxicity, enzyme activation, edema, and inflammation (Trends Pharmacol Sci. 1996; 17:227-233, Crit Care Med. 1988; 16:954-963).

Furthermore, systemic-derived inflammation has recently been shown to cause BBB tight junctional disruption and increased paracellular permeability. The BBB is capable of rapid modulation in response to physiological stimuli at the cytoskeletal level, which enables it to protect the brain parenchyma and maintain a homeostatic environment.

Research has shown that destruction of the BBB is associated with diseases of the CNS. However, there is little research on how the BBB might be protected.

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

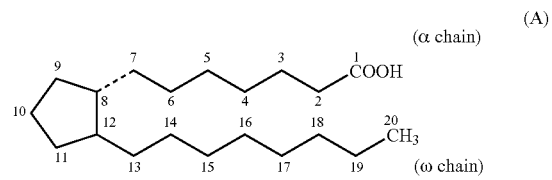

On the other hand, some of synthetic analogues of primary PGs have modified skeletons. The primary PGs are classified into PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β-type (the hydroxyl group is of a β-configuration).

$PGE_1$ and $PGE_2$ and $PGE_3$ are known to have vasodilation, hypotension, gastric secretion decreasing, intestinal tract movement enhancement, uterine contraction, diuretic, bronchodilation and anti ulcer activities. $PGF_{1\alpha}$, $PGF_{2\alpha}$ and $PGF_{3\alpha}$ have been known to have hypertension, vasoconstriction, intestinal tract movement enhancement, uterine contraction, lutein body atrophy and bronchoconstriction activities.

Some 15-keto (i.e., having oxo at the 15-position instead of hydroxy)-PGs and 13,14-dihydro (i.e., having single bond between the 13 and 14-position)-15-keto-PGs are known as the substances naturally produced by the action of enzymes during the metabolism of primary PGs.

U.S. Pat. No. 5,290,811 to Ueno et al. describes that some 15-keto-PG compounds are useful for improvement of encephalic function. U.S. Pat. No. 5,290,811 indicates that when the bond between 13- and 14-positions is saturated, a keto-hemiacetal equilibrium may sometimes be formed by the formation of a hemiacetal between the hydroxy group at 11-position and the keto group at 15-position.

U.S. Pat. No. 5,317,032 to Ueno et al. describes prostaglandin compound cathartics, including the existence of bicyclic tautomers and U.S. Pat. No. 6,414,016 to Ueno describes the bicyclic tautomers as having pronounced activity as anti-constipation agents. The bicyclic tautomers, substituted by one or more halogen atoms can be employed in small doses for relieving constipation. At the C-16 position, especially, fluorine atoms can be employed in small doses for relieving constipation.

SUMMARY OF THE INVENTION

The present inventor conducted an intensive study and found that 11-deoxy-prostaglandin compounds possessed significant effects on the central nervous system disorders, which resulted in the completion of the present invention.

Namely, the present invention relates to a method for treating a central nervous system disorder in a mammalian subject, which comprises administering an effective amount of a 11-deoxy-prostaglandin compound to a subject in need thereof.

The present invention further relates to a composition for treating a central nervous system disorder in a mammalian subject, which comprises an effective amount of a 11-deoxy-prostaglandin compound.

Furthermore, the present invention relates to a use of 11-deoxy-prostaglandin compound for manufacturing a composition for treating a central nervous system disorder in a mammalian subject, which comprises an effective amount of a 11-deoxy-prostaglandin compound.

Another embodiment of the present invention relates to a method for protecting cerebrovascular endothelial cells in a mammalian subject, which comprises administering an effective amount of a 11-deoxy-prostaglandin compound to a subject in need thereof.

In another aspect of the present invention, a novel compound represented by the formula (IV):

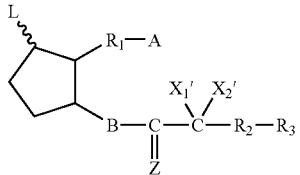

(IV)

wherein L is hydrogen, hydroxy, halogen, lower alkyl, hydroxy(lower)alkyl, lower alkanoyloxy or oxo; wherein the five-membered ring may optionally have at least one double bond;

A is —CH$_3$, —CH$_2$OH, —COCH$_2$OH, —COOH or a functional derivative thereof;

B is single bond, —CH$_2$—CH$_2$—, —CH═CH—, —C≡C—, —CH$_2$—CH$_2$—CH$_2$—, —CH═CH—CH$_2$—, —CH$_2$—CH═CH—, —C≡C—CH$_2$— or —CH$_2$—C≡C—;

Z is

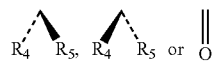

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$' and X$_2$' are same or different halogen atoms;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one of carbon atom in the aliphatic hydrocarbon is optionally substituted by oxygen, nitrogen or sulfur;

provided that the formula (IV) is not 11-deoxy-13,14-dihydro-15-keto-16,16-difluoro-PGE$_1$ is provided.

DETAILED DESCRIPTION OF THE INVENTION

Figure 1:
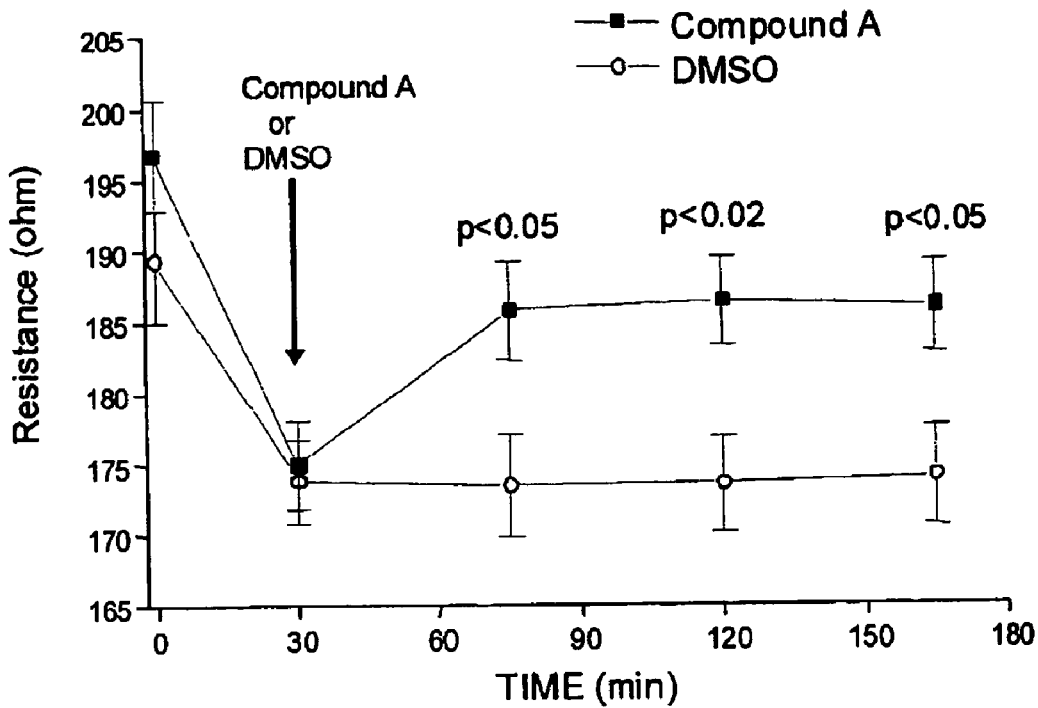
FIG. 1 is a graph showing the effect of Compound A on Recovery of Transendothelial Electrical Resistance (TEER). Human vascular endothelial cell cultures were brought to confluence, as measured by transendothelial electrical resistance (TEER). The cell cultures were then deprived of oxygen for 30 minutes by incubation in a nitrogen atmosphere. The cells were then either treated with 0.1% DMSO or with 5 nM Compound A with 0.1% DMSO. Statistical significance is indicated at all data points after drug treatment. N=10 cells.

In the present invention, the "11-deoxy-prostaglandin compound" (hereinafter, referred to as "11-deoxy-PG compound") may include any derivatives or analogs (including substituted derivatives) of a compound having no substituent at 11-position of the prostanoic acid skeleton, irrespective of the configuration of the five-membered ring, the number of double bonds, presence or absence of a substituent, or any other modification in the α or ω chain.

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

As stated above, the nomenclature of the 11-deoxy-PG compounds is based on the prostanoic acid skeleton. However, in case the compound has a similar partial structure as a prostaglandin, the abbreviation of "PG" may be used. Thus, a 11-deoxy-PG compound of which α-chain is extended by two carbon atoms, that is, having 9 carbon atoms in the α-chain is named as 2-decarboxy-2-(2-carboxyethyl)-11-deoxy-PG compound. Similarly, 11-deoxy-PG compound having 11 carbon atoms in the α-chain is named as 2-decarboxy-2-(4-carboxybutyl)-11-deoxy-PG compound. Further, 11-deoxy-PG compound of which ω-chain is extended by two carbon atoms, that is, having 10 carbon atoms in the ω-chain is named as 11-deoxy-20-ethyl-PG compound. These compounds, however, may also be named according to the IUPAC nomenclatures.

Examples of the analogs (including substituted derivatives) or derivatives include a 11-deoxy-PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substuents at position 5 include halogen atoms such as chlorine and fluorine. Preferred substituents at position 6 include an oxo group forming a carbonyl group. Stereochemistry of PGs having hydroxy, lower alkyl or hydroxy(lower) alkyl substituent at position 9 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

The nomenclature of the 11-deoxy-PG compounds used herein is based on the numbering system of the prostanoic acid represented in the above formula (A).

A preferred compound used in the present invention is represented by the formula (I):

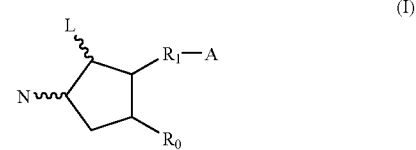

wherein L and N are hydrogen, hydroxy, halogen, lower alkyl, hydroxy(lower)alkyl, lower alkanoyloxy or oxo, wherein the five-membered ring may optionally have at least one double bond;

A is —CH$_3$, —CH$_2$OH, —COCH$_2$OH, —COOH or a functional derivative thereof;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and R$_0$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower) alkyloxy; aryl; aryloxy; heterocyclic group; heterocyclic-oxy group, and at least one of carbon atom in the aliphatic hydrocarbon is optionally substituted by oxygen, nitrogen or sulfur.

A more preferred compound used in the present invention is represented by the formula (II):

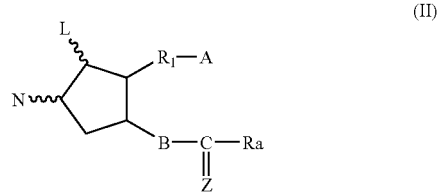

wherein L and N are hydrogen, hydroxy, halogen, lower alkyl, hydroxy(lower)alkyl, lower alkanoyloxy or oxo, wherein the five-membered ring may optionally have at least one double bond;

A is —CH$_3$, —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one of carbon atom in the aliphatic hydrocarbon is optionally substituted by oxygen, nitrogen or sulfur.

A group of particularly preferable compounds among the above-described compounds is represented by the formula (III):

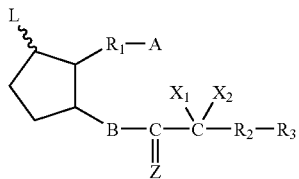

(III)

wherein L is hydrogen, hydroxy, halogen, lower alkyl, hydroxy(lower)alkyl, lower alkanoyloxy or oxo, wherein, and the five-membered ring may optionally have at least one double bond;

A is —CH$_3$, —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and R$_2$ is a single bond or lower alkylene; and R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one of carbon atom in the aliphatic hydrocarbon is optionally substituted by oxygen, nitrogen or sulfur.

The present invention further relates to a compound represented by the formula (IV):

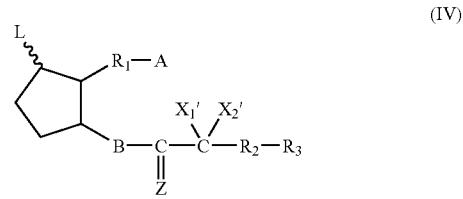

(IV)

wherein L is hydrogen, hydroxy, halogen, lower alkyl, hydroxy(lower)alkyl, lower alkanoyloxy or oxo, wherein the five-membered ring may optionally have at least one double bond;

A is —CH$_3$, —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$' and X$_2$' are same or different halogen atoms;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one of carbon atom in the aliphatic hydrocarbon is optionally substituted by oxygen, nitrogen or sulfur;

provided that the formula (IV) is not 11-deoxy-13,14-dihydro-15-keto-16,16-difluoro-PGE$_1$, and a method for producing the same.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 6 to 10 carbon atoms for $R_1$ and 1 to 10, especially 1 to 8 carbon atoms for $R_a$.

The term "halogen" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen atom, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred examples of L include hydroxy or oxo which has a 5-membered ring structure of, so called, especially PGF or PGE type.

Preferred example A is —COOH, its pharmaceutically acceptable salt, ester or amide thereof.

Preferred example B is —$CH_2$—$CH_2$—, which provide the structure of so-called, 13,14-dihydro type.

Preferred example of $X_1$ and $X_2$ is hydrogen, or that at least one of them is halogen, more preferably, both of them are halogen, especially, fluorine that provides a structure of, so called 16,16-difluoro type.

Preferred $X_1'$ and $X_2'$ are difluoro atoms.

Preferred $R_1$ is a hydrocarbon containing 1-10 carbon atoms, preferably, 6-10 carbon atoms. Further, at least one of carbon atom in the aliphatic hydrocarbon is optionally substituted by oxygen, nitrogen or sulfur.

Examples of $R_1$ include, for example, the following groups:
—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—, —CH$_2$—CH$_2$—CH$_2$—CH$_2$—CH(CH$_3$)—CH$_2$—,
—CH$_2$—CH$_2$—CH$_2$—CH$_2$—O—CH$_2$—,
—CH$_2$—CH=CH—CH$_2$—O—CH$_2$—,
—CH$_2$—C≡C—CH$_2$—O—CH$_2$—,
—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—,
—CH$_2$—CH$_2$—CH$_2$—CH$_2$—CH$_2$—CH=CH—,
—CH$_2$—C≡C—CH$_2$—CH$_2$—CH$_2$—CH$_2$—,
—CH$_2$—CH$_2$—CH$_2$—CH$_2$—CH$_2$—CH(CH$_3$)—CH$_2$—,
—CH$_2$—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—CH$_2$—,
—CH$_2$—CH$_2$—CH$_2$—CH$_2$—CH$_2$—CH$_2$—CH=CH—,
CH$_2$—C≡C—CH$_2$—CH$_2$—CH$_2$—CH$_2$—CH$_2$—,
—CH$_2$—CH$_2$—CH$_2$—CH$_2$—CH$_2$—CH$_2$—CH (CH$_3$)—CH$_2$—

Preferred Ra is a hydrocarbon containing 1-10 carbon atoms, more preferably, 1-8 carbon atoms. Ra may have one or two side chains having one carbon atom.

Preferred R$_2$ is single bond, and preferred R$_3$ is lower alkyl. R3 may have one or two side chains having one carbon atom.

The configuration of the ring and the α- and/or ω chains in the above formula (I), (II), (III) and (IV) may be the same as or different from that of the primary PGs. However, the present invention also includes a mixture of a compound having a primary type configuration and a compound of a non-primary type configuration.

The typical example of the present compound is a 11-deoxy-13,14-dihydro-16,16-difluoro-PGE or PGF compound, 11-deoxy-13,14-dihydro-15-keto-16,16-difluoro-PGE or PGF compound, 2-decarboxy-2-(2-carboxyethyl)-11-deoxy-13,14-dihydro-15-keto-16,16-difluoro-PGE or PGF compound, or 11-deoxy-13,14-dihydro-15-keto-16,16-difluoro-20-methyl or ethyl-PGE or PGF compound and its derivative or analogue.

The preferred example of the present compound is 11-deoxy-13,14-dihydro-15-keto-16,16-difluoro-PGE$_1$, 11-deoxy-13,14-dihydro-16,16-difluoro-PGE$_1$, 11-deoxy-13,14-dihydro-15-keto-16,16-difluoro-PGE$_1$ isopropyl ester, 2-decarboxy-2-(2-carboxyethyl)-11-deoxy-13,14-dihydro-15-keto-16,16-difluoro-PGE$_1$ isopropyl ester, 2-decarboxy-2-(2-carboxyethyl)-11-deoxy-13,14-dihydro-15-keto-16,16-difluoro-PGE$_1$, 11-deoxy-13,14-dihydro-15-keto-16,16-difluoro-20-methyl-PGE$_1$ isopropyl ester, 11-deoxy-13,14-dihydro-15-keto-16,16-difluoro-20-methyl-PGE$_1$, 11-deoxy-13,14-dihydro-15-keto-16,16-difluoro-20-ethyl-PGE$_1$, 11-deoxy-13,14-dihydro-15-keto-16,16-difluoro-PGE$_1$ methyl ester, 11-deoxy-13,14-dihydro-15-keto-16,16-difluoro-20-ethyl-PGE$_1$ isopropyl ester or 11-deoxy-13,14-dihydro-15-keto-16,16-difluoro-PGF$_{1\alpha}$ isopropyl ester.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 (these cited references are herein incorporated by reference).

According to the present invention, a mammalian subject may be treated by the instant invention by administering the compound used in the present invention. The subject may be any mammalian subject including a human. The compound may be applied systemically or topically. Usually, the compound may be administered by oral administration, intravenous injection (including infusion), subcutaneous injection, intra rectal administration, intra vaginal administration, transdermal administration and the like.

The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.0001-500 mg/kg per day, more preferably 0.0001-100 mg/kg.

The compound may preferably be formulated in a pharmaceutical composition suitable for administration in a conventional manner. The composition may be those suitable for oral administration, injection or perfusion as well as it may be an external preparation, suppository or pessary.

The composition of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin, and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.000001-10.0%, more preferably 0.00001-5.0%, most preferably 0.0001-1%.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary.

They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluentseg. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Examples of the injectable compositions of the present invention for parenteral administration include sterile aqueous or non-aqueous solutions, suspensions and emulsions.

Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e. g. a bacteria-retaining filter, compounding with a sterilizer, or by means of gas or radioisotope irradiation sterilization.

The injectable composition may also be provided as a sterilized powder composition to be dissolved in a sterilized solvent for injection before use.

The external preparation of the invention may be any form of the external preparations used in the fields of dermatology and otolaryngology, which includes ointment, cream, lotion and spray.

Another form of the composition is suppository or pessary, which may be prepared by mixing active ingredients into a conventional base such as cacao butter that softens at body temperature, and nonionic surfactants having suitable softening temperatures may be used to improve absorbability.

The term "treatment" used herein includes any means of control such as care, relief, attenuation, and arrest.

The term "central nervous system disorder" used herein includes any central nervous system disorder involved or being associated with any type of condition and/or diseases, or caused by ischemia, trauma, infection, inflammation, tumor, edema, hypotension, hypoxemia, blood clot (thrombus), enzyme activation, arterial obstruction (embolus), arteriosclerosis, metabolic disorder, degeneration, aging, drugs, medications or surgical procedures.

Examples of "central nervous system disorder" include, but not limited to, cerebrovascular disorders such as stroke and cerebral infarction (e.g., cerebral thrombosis, cerebral embolism, lacunar cerebral infarction, asymptomatic cerebral infarction); vasospasm due to intracerebral hemorrhage or subarachnoid hemorrhage; cerebrovascular dementia; neuronal disorders such as Alzheimer disease, Parkinson's disease, Huntington's chorea, dementia, Pick disease, spinocerebellar degeneration, chorea, AIDS encephalopathy, hepatic encephalopathy, amyotrophic lateral sclerosis, anticancer drug-induced peripheral neuropathy, diabetic neuropathy, traumatic neurological disorder and multiple sclerosis; cerebral edema, hypernatremic cerebral disorder and brain tumor; ischemic diseases such as cerebral ischemia caused by vascular disorders, transient ischemic attack (TIA), reversible ischemic neurological deficit (RIND), cerebrovascular ischemia caused by migraine or cocaine abuse, cerebral ischemia including epilepsy or epileptic psychiatric symptoms, cerebral ischemia during surgical operation (ischemic tissue injury), cerebral ischemia caused by head injury, cerebral ischemia due to hypotension, hypoxemia or dyspnea and cerebral ischemia due to cardiac arrest; inflammatory cerebral disorders such as choronic relapsing multiple sclerosis, encephalomyelitis, meningitis, traumatic brain injury; neonatal asphyxia and secondary complications of these diseases.

According to the present invention, the compounds used herein have a significant effect on recovery of barrier function of cerebrovascular endothelial cells, especially blood brain barrier, so it is also useful for protecting cerebrovascular endothelial cells.

The pharmaceutical composition of the present invention may further contain other pharmacological ingredients as far as they do not contradict the purpose of the present invention.

The present formulations may contain a single active ingredient or a combination of two or more active ingredients. In a combination of plural active ingredients, their respective contents may be suitably increased or decreased in consideration of their therapeutic effects and safety.

Further, the present formulations may contain other pharmacologically active ingredients, as far as they are not contrary to the objects of the present invention.

The present invention will be described in detail with reference to the following examples, which, however, are not intended to limit the scope of the present invention.

Example 1

Method

Four-week-old male ddY mice were housed in aluminum cages in an animal room controlled for temperature (24±3° C.), relative humidity (55±10%), ventilation rate (~12 times/hour) and light-dark cycle (fluorescent lighting: 8:00 to 20:00) for at least 7 days. The animals were allowed free access to pellet diet and tap water from water bottles. Healthy animals without abnormalities in general signs were used in this study.

11-deoxy-13,14-dihydro-15-keto-16,16-difluoro-$PGE_1$ (hereinafter, "Compound A") was dissolved in a vehicle (physiologic saline containing 0.01% polysorbate 80 and 0.5% ethanol), and was administered subcutaneously to the animals. The control group received an equal amount of the vehicle in the same manner.

The animals were decapitated at 30 minutes after the administration, and the persistent time of gasping movements was measured.

Results

As shown in Table 1, Compound A at 10, 30, 100 and 300 μg/kg produced a dose-dependent prolongation of the persistent time of gasping movement after decapitation. The results indicate that Compound A has a neuroprotective activity and that Compound A is useful for the treatment of ischemic disease.

TABLE 1

Effects of Compound A on Persistent Time of Gasping Movements after Decapitation in Mice

| Group | Dose Level (μg/kg) | Dose Route | No. of Animals | Persistent Time of Gasping Movements (sec, Mean ± SE) |
|---|---|---|---|---|
| Control (Vehicle) | 0 | s.c. | 10 | 20.7 ± 0.6 |
| Compound A | 10 | s.c. | 10 | 21.7 ± 0.6 |
| Compound A | 30 | s.c. | 10 | 22.0 ± 0.4 |
| Compound A | 100 | s.c. | 10 | 23.2 ± 0.8* |
| Compound A | 300 | s.c. | 10 | 23.6 ± 0.6** | s.c.: subcutaneous,
**$p < 0.01$,
*$p < 0.05$ compared to vehicle-treated control group (Dunnett's multiple comparison test).

Example 2

Method

Four-week-old male ddY mice were housed in aluminum cages in an animal room controlled for temperature (24±3° C.), relative humidity (55±10%), ventilation rate (~12 times/hour) and light-dark cycle (fluorescent lighting: 8:00 to 20:00) for at least 7 days. The animals were allowed free access to pellet diet and tap water from water bottles. Healthy animals without abnormalities in general signs were used in this study. The animals were fasted for 20 hours or longer with free access to water before use.

Compound A and 11-deoxy-13,14-dihydro-15-keto-16,16-difluoro-PGE$_1$ methyl ester (hereinafter, "Compound B") were dissolved in a vehicle (physiologic saline containing 0.01% polysorbate 80 and 0.5% ethanol), and was administered orally to the animals. The control group received an equal amount of the vehicle in the same manner.

The animals were decapitated at 30 minutes after the administration, and the persistent time of gasping movements was measured.

<Results>

As shown in Table 2, oral administration of Compound A and Compound B at 100, 300 and 1000 µg/kg produced a dose-dependent prolongation of the persistent time of gasping movement after decapitation. The results indicate that Compound A and Compound B have a neuroprotective activity by oral administration and that Compound A and Compound B are useful for the treatment of ischemic disease.

TABLE 2

Effects of Oral Administration of Compound A and B on Persistent Time of Gasping Movements after Decapitation in Mice

| Group | Dose Level (µg/kg) | Dose Route | No. of Animals | Persistent Time of Gasping Movements (sec, Mean ± SE) |
|---|---|---|---|---|
| Control (Vehicle) | 0 | p.o. | 10 | 17.6 ± 0.4 |
| Compound A | 100 | p.o. | 10 | 18.8 ± 0.5 |
| Compound A | 300 | p.o. | 10 | 18.9 ± 0.3 |
| Compound A | 1000 | p.o. | 10 | 20.2 ± 0.6** |
| Compound B | 100 | p.o. | 10 | 17.6 ± 0.5 |
| Compound B | 300 | p.o. | 10 | 19.1 ± 0.5 |
| Compound B | 1000 | p.o. | 10 | 19.1 ± 0.4 | p.o.: per os,
**p < 0.01,
*p < 0.05 compared to vehicle-treated control group (Dunnett's multiple comparison test).

Example 3

Method

Four-week-old male ddY mice were housed in aluminum cages in an animal room controlled for temperature (24±3° C.), relative humidity (55±10%), ventilation rate (~12 times/hour) and light-dark cycle (fluorescent lighting: 8:00 to 20:00) for at least 7 days. The animals were allowed free access to pellet diet and tap water from water bottles. Healthy animals without abnormalities in general signs were used in this study.

11-deoxy-13,14-dihydro-16,16-difluoro-PGE$_1$ (hereinafter, "Compound C") was dissolved in a vehicle (physiologic saline containing 0.01% polysorbate 80 and 0.5% ethanol), and was administered subcutaneously to the animals. The control group received an equal amount of the vehicle in the same manner.

The animals were decapitated at 30 minutes after the administration, and the persistent time of gasping movements was measured.

<Results>

As shown in Table 3, Compound C at 300 µg/kg produced a significant prolongation of the persistent time of gasping movement after decapitation. The results indicate that Compound C has a neuroprotective activity.

TABLE 3

Effect of Compound C on Persistent Time of Gasping Movements after Decapitation in Mice

| Group | Dose Level (µg/kg) | Dose Route | No. of Animals | Persistent Time of Gasping Movements (sec, Mean ± SE) |
|---|---|---|---|---|
| Control (Vehicle) | 0 | s.c. | 10 | 21.9 ± 0.5 |
| Compound C | 300 | s.c. | 10 | 25.2 ± 0.7** | s.c.: subcutaneous,
**p < 0.01 compared to vehicle-treated control group.

Example 4

Method

Seven-week-old Crj: CD (SD) male rats were housed in polymethylpentene cages in an animal room controlled for room temperature (22-26° C.), relative humidity (47-60%), ventilation rate (10-20 times/hour) and light-dark cycle (lighting: 7:00 to 19:00) for at least 6 days. The animals were allowed free access to pellet diet and water from water bottles. Animals judged to be in good health were used in this study.

Rats were anesthetized by inhalation of a gas mixture of 2% isoflurane and $N_2O:O_2$ (=7:3), stabilized in the supine position, and maintained in the anesthetized state by inhalation of the above gas mixture. The animals were monitored for rectal temperature using a temperature probe during the period of the surgical operation. When a fall in body temperature was observed, an incandescent lamp was used to maintain the temperature at around 37° C. The right common carotid artery, external carotid artery, and internal carotid artery were exposed for occluding the middle cerebral artery (hereafter, MCA). The right common carotid artery and the external carotid artery were ligatured using sutures (5-0), and a 19 mm-long segment of No. 4-0 nylon suture which were precoated with silicone was inserted into the MCA through the bifurcation of the external and internal carotid arteries to occlude the MCA. At 2 hours after the MCA occlusion, the suture was removed and the blood flow in the MCA was restored.

Compound A was dissolved in a vehicle (physiological saline containing 1% polysorbate 80), and was administered intravenously to the animals at a volume of 2 mL/kg immediately after the MCA occlusion-reperfusion and 30 minutes after the MCA occlusion-reperfusion. The control group received an equal volume of the vehicle in the same manner.

At 24 hours after MCA occlusion, the animals were decapitated and the brains were immediately isolated. Using a tissue chopper (Micro-3D; The Mickle Laboratory Engineering Co., Ltd.), sequential brain sections 2 mm in thickness were prepared. The brain tissue sections were positioned following the brain atlas of Paxinos and Watson to include the coronal plane at 4 mm anterior to the bregma, at 2 mm anterior to the bregma, at the bregma, at 2 mm posterior to the bregma, at 4 mm posterior to the bregma, and at 6 mm posterior to the bregma. The brain sections were stained in 1% TTC solution and photographed. Graphic analysis (Adobe Photoshop™, version 3.0 J; Adobe Systems Incorporated, Color Count 0.3b; K&M Software Corporation) was applied to the photographs, and the infarct area was measured. Based on these results, the infarct volume (4 mm anterior to the bregma—6 mm posterior to the bregma) was calculated using the following formula.

$$V = 2(a+b)/2 + 2(b+c)/2 + 2(c+d)/2 + 2(d+e)/2 + 2(e+f)/2$$
$$= a + 2(b+c+d+e) + f$$

V: infarct volume
a: infarct area at the cross-section 4 mm before the bregma
b: infarct area at the cross-section 2 mm before the bregma
c: infarct area at the cross-section just at the bregma
d: infarct area at the cross-section 2 mm behind the bregma
e: infarct area at the cross-section 4 mm behind the bregma
f: infarct area at the cross-section 6 mm behind the bregma <Results>

As shown in Table 4, Compound A at 0.05 and 0.5 mg/kg significantly reduced the cerebral infarct volume after ischemia in a dose-dependent manner compared with that in the vehicle group. The results indicate that Compound A is useful for the treatment of cerebrovascular disorders such as cerebral infarct.

TABLE 4

Effects of Compound A on cerebral infarct volume after transient focal cerebral ischemia in rats

| Group | Dose mg/kg | n | Infarct volume mm$^3$ |
|---|---|---|---|
| Control (Vehicle) | — | 10 | 280.8 ± 16.2 |
| Compound A | 0.05 | 10 | 208.2 ± 22.2* |
| Compound A | 0.5 | 10 | 172.9 ± 25.5** |

Brain was removed at 24 hours after MCA occlusion. Each value represents the mean±S.E. of 10 rats. Compounds were administered intravenously immediately after MCA occlusion-reperfusion and 30 minutes after MCA occlusion-reperfusion. *P<0.05, **P<0.01; Significant difference from vehicle group and Compound A group (Dunnett's multiple comparison test)

Example 5

Method

Alzheimer's disease model animals were prepared by bilateral ibotenic acid lesions of basal ganglia in rats. Briefly, rats were anesthetized with pentobarbital sodium and placed in a small animal stereotaxic apparatus. Bilateral infusions of 5 µg/0.5 µL of ibotenic acid into the basal ganglia were made at a rate of 0.1 µL/min via a syringe pump and a stainless steel cannula (outer diameter: 0.5 mm). Stereotaxic coordinates were as follows: −0.8 mm posterior from bregma, 2.6 mm lateral (both sides) from midline, and 7.4 mm depth from the bone surface. Animals in sham group received only anesthesia. Animals were then housed with free access to food and water for the rest of the study.

Compound A was orally administered for 14 days after surgery to the model animals. Control group received the same amount of the vehicle.

Morris water maze test was performed to evaluate the effect of test compound. The water maze was a circular pool (painted gray, 1.48 m in diameter, 0.33 m high). The pool contained water that was maintained at a temperature of 17-18° C. During testing in the water maze, a platform, 12 cm in diameter, was located 2 cm below the water in one of four locations (zone 4) in the pool, approximately 38 cm from the sidewall. A light bulb was placed around the pool as a cue external to the maze. The animals received 2 trials per day from 10 days after the initiation of the administration with Compound A or the vehicle. The rats were trained to locate the hidden escape platform, which remained in a fixed location throughout testing. Trials lasted a maximum of 90 sec. The latency to find the submerged platform was recorded and used as a measure of acquisition of the task. The animals were tested in this way for 4 days (total 8 trials), and then they received a probe trial on the 5th day. For the probe trial, the platform was removed from the pool and then the animal was released from the quadrant opposite to where the platform would have been located. The length of the trial was 90 sec, after which the rat was removed from the pool. The time the rat spent searching for the platform in the training quadrant (zone 4): i.e., the previous location of the platform was recorded and used as an index of memory.

<Results>

As shown in table 5 and 6, vehicle group showed severely impaired spatial cognition. Treatment with Compound A produced significant reversals of the deficit in learning and memory. These results suggest that Compound A is useful for the treatment of neuronal disorders such as Alzheimer's disease.

TABLE 5

Effect of Compound A on goal latency in Morris water maze learning test.

| Group | Dose mg/kg | n | Goal latency (8$^{th}$ trial) mean ± SE, sec |
|---|---|---|---|
| Sham | 0 | 10 | 24.6 ± 2.7 |
| Vehicle | 0 | 10 | 90.0 ± 0.0## |
| Compound A | 1 | 10 | 51.5 ± 13.7** | p < 0.01 compared with sham group,
**p < 0.01 compared with vehicle group

TABLE 6

Effect of Compound A on time spent in quadrant (zone 4) where previous location of the platform in Morris water maze learning test.

| Group | Dose mg/kg | n | Time spent in zone 4 mean ± SE, sec |
|---|---|---|---|
| Sham | 0 | 10 | 24.5 ± 2.0 |
| Vehicle | 0 | 10 | 12.2 ± 1.5## |
| Compound A | 1 | 10 | 20.8 ± 3.6* | p < 0.01 compared with sham group,
*p < 0.05 compared with vehicle group

Example 6

Method

Human vascular endothelial cell cultures were brought to confluence, as measured by transendothelial electrical resistance (TEER). The cell cultures were then deprived of oxygen for 30 minutes by incubation in a nitrogen atmosphere. The cells were then either treated with 0.1% DMSO or with 5 nM Compound A with 0.1% DMSO final.

Results

As shown FIG. 1, the DMSO-treated cells showed very little recovery of TEER. The Compound A-treated cells showed immediate recovery of TEER.

The results demonstrate that TEER, a measured barrier function of endothelial cells, recovers rapidly from damage after Compound A-treatment.

Example 7

Method

Human microvascular endothelial cells (adult) (HMVEC-AD) were grown to confluence. The cells were then treated for 30 minutes with a nitrogen atmosphere and returned to normal oxygen. ATP levels were monitored at the indicated time points using a luciferin-luciferase assay system (AT-Plite, Perkin Elmer).

Results

Figure 2:
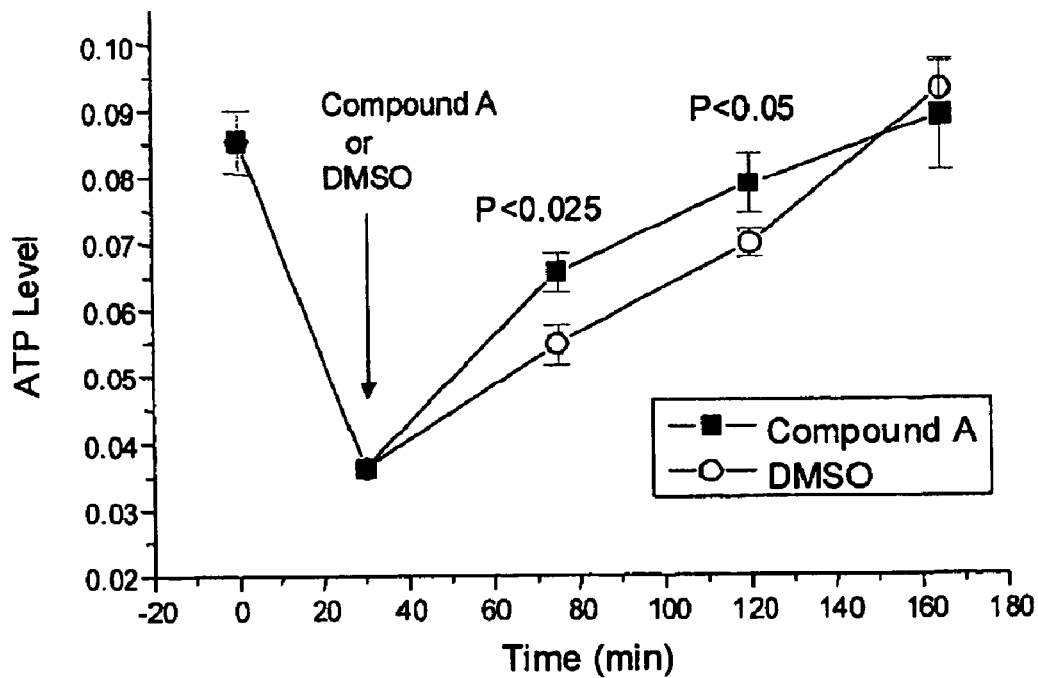
FIG. 2 is a graph showing the effect of Compound A on Recovery of ATP Level. Human microvascular endothelial cells (adult) (HMVEC-AD) were grown to confluence. The cells were then treated for 30 minutes with a nitrogen atmosphere and returned to normal oxygen. ATP levels were monitored at the indicated time points using a luciferin-luciferase assay system (ATPlite, Perkin Elmer). ATP levels are given as relative luminescence. N=6 cells at each time point.

As shown in FIG. 2, ATP levels decreased when the cells were exposed to a nitrogen atmosphere for 30 minutes. ATP levels returned more quickly in cells treated with 5 nM Compound A compared to cells treated with 0.01% DMSO alone.

The results indicate that the Compound A is useful for the treatment of central nervous system disorders.

Synthesis Example 1

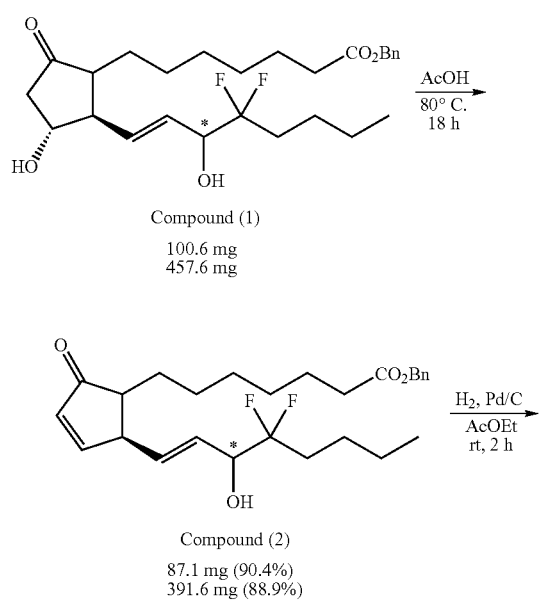

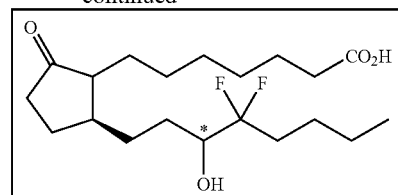

Compound (3)
57.6 mg (91.7%)
298.5 mg (95.7%)

Synthesis of 16,16-difluoro-PGA$_1$ benzyl ester (2)

16,16-Difluoro-PGE$_1$ benzyl ester (1) (457.8 mg, 0.95 mmol) was dissolved in acetic acid (13.7 mL, 0.24 mol), and the solution was stirred at 80° C. for 18 hours. The reaction mixture was cooled to room temperature. 10 mL of toluene was added to the solution and concentrated under reduced pressure. This operation was repeated five times to removed acetic acid. The residue was purified by silica gel column chromatography (silica gel: FL60D (70 g), Fuji Silysia, hexane/ethyl acetate (2:1)) to obtain compound (2) as yellow oil. Yield: 391.6 mg (88.9%).

Synthesis of 11-deoxy-13,14-dihydro-16,16-difluoro-PGE$_1$ (3)

16,16-Difluoro-PGA$_1$ benzyl ester (compound (2)) (382.5 mg, 0.83 mmol) was hydrogenated in ethyl acetate (10 mL) under the presence of 10% palladium-carbon (57.4 mg, wet with 50% w/w of water) at room temperature, at atmospheric pressure for 2 hours. The reaction mixture was filtered through a Celite pad, the filter cake was washed with ethyl acetate, and then the filtrate was concentrated under reduced pressure. The residue was purified by silica gel column chromatography (silica gel BW-300SP (50 g, wet with 15% w/w of water), Fuji Silysia, hexane/ethyl acetate (1:1)) to obtain crude compound (3) (298.5 mg, 95.7%).

The crude compound (3) was combined with another lot of the crude compound. And then, totally about 350 mg of the crude compound was purified by preparative HPLC (YMC-Pack D-SIL-5-06 20×250 mm, hexane/2-propanol/acetic acid (250:5:1), 20 mL/min) to obtain compound (3) as colorless oil. Yield: 297.3 mg (HPLC purification recovery: 83.5%).

$^1$H-NMR (200 MHz, CDCl$_3$) δ 0.94 (3H, t, J=7.1 Hz), 1.22-2.29 (28H, m), 2.34 (2H, t, J=7.3 Hz), 3.65-3.81 (1H, m)

$^{13}$C-NMR (50 MHz, CDCl$_3$) δ 13.70, 22.40, 23.25, 24.32, 26.28, 26.63), 27.18, 27.58, 28.49, 29.09, 30.39, 31.77 (t, J=24.4 Hz), 33.67, 37.63, 41.05, 54.76, 72.73 (t, J=29.0 Hz), 124.09 (t, J=244.3 Hz), 179.07, 220.79.

Synthesis Example 2

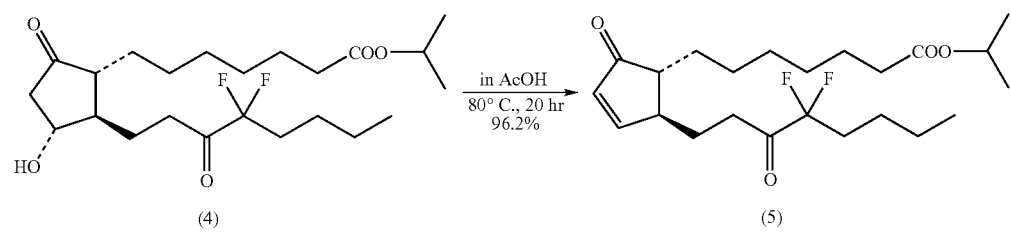

-continued

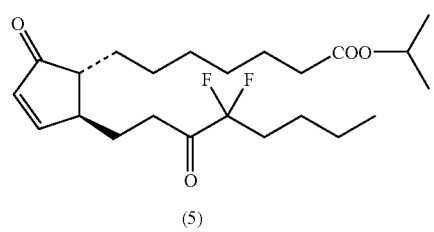
(5)

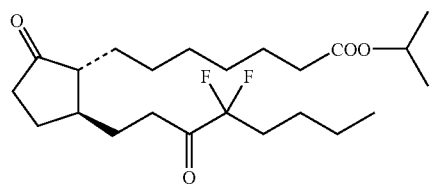
pure (6)

Figure 3:
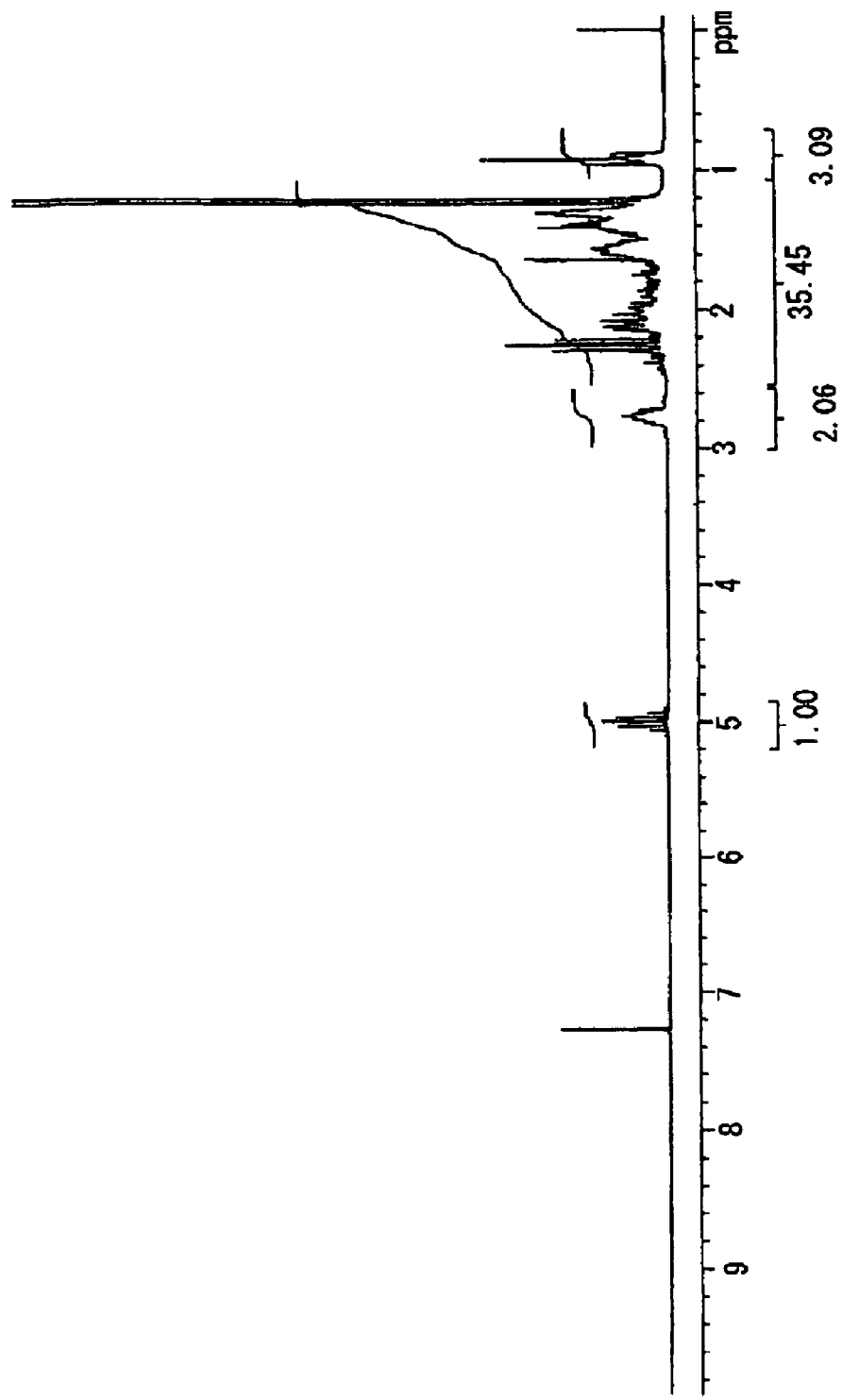
FIG. 3 is a $^1$H-NMR (200 MHz, CDCl$_3$) chart of the compound (6) obtained in Synthesis Example 2 below.
Figure 4:
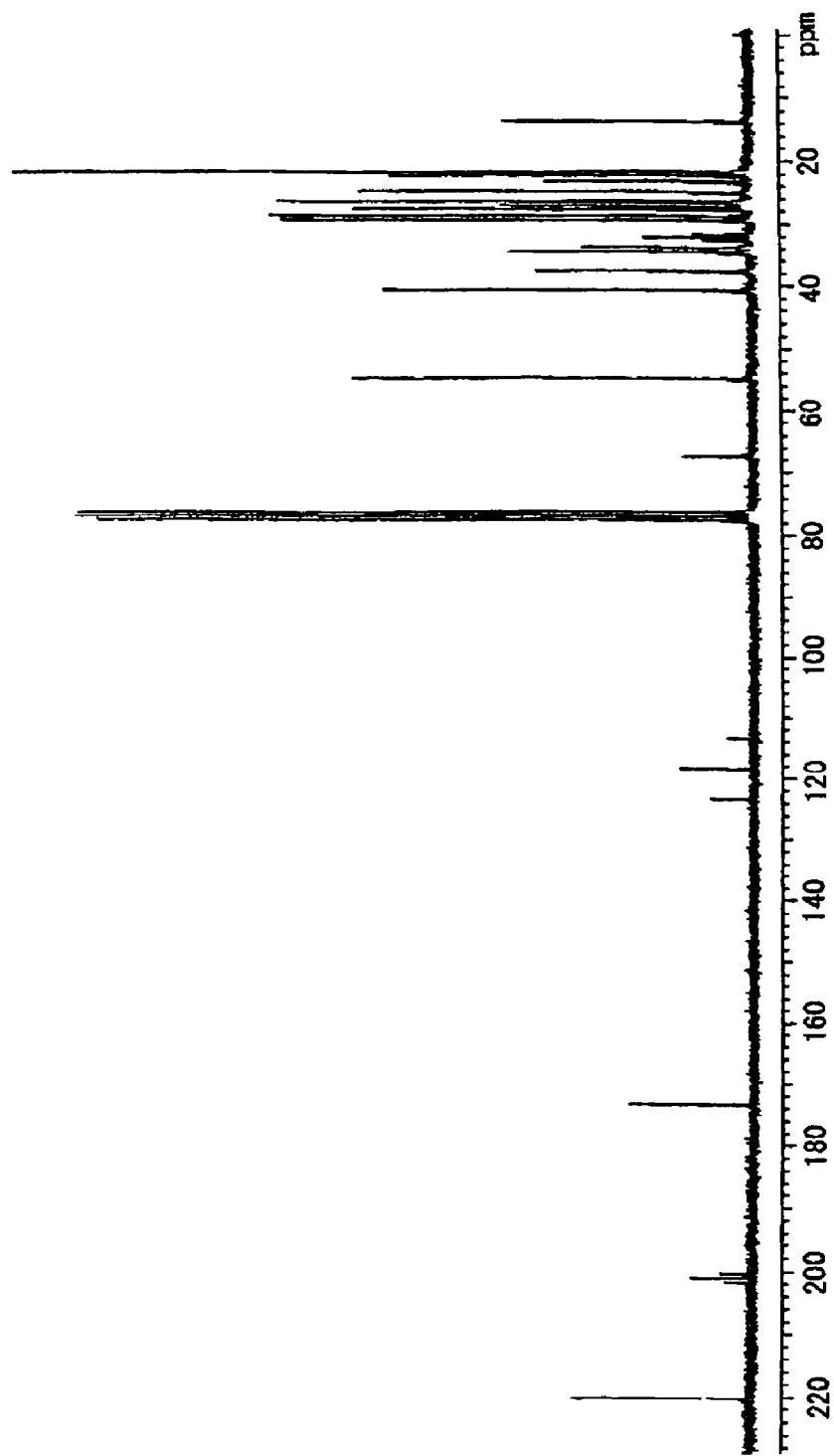
FIG. 4 is a $^{13}$C-NMR (50 MHz, CDCl$_3$) chart of the compound (6) obtained in Synthesis Example 2 below.

According to the similar manner described in Synthesis Example 1, 11-deoxy-13,14-dihydro-15-keto-16,16-difluoro-PGE$_1$ isopropyl ester (Compound (6)) was obtained as colorless oil by the above two-step reaction. Yield: 0.285 g (1$^{st}$ step: 96.2%, 2$^{nd}$ step: 97.6%, HPLC purification: recovery 81.0%). $^1$H-NMR (200 MHz, CDCl$_3$) and $^{13}$C-NMR (50 MHz, CDCl$_3$) of the Compound (6) are shown in FIGS. 3 and 4 respectively.

Synthesis Example 3

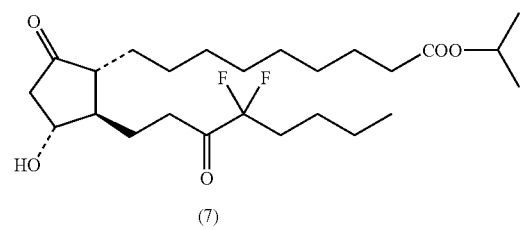
(7)

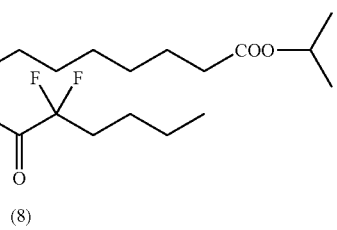
(8)

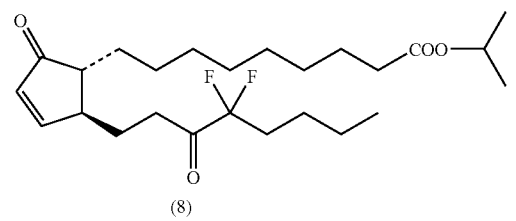
(8)

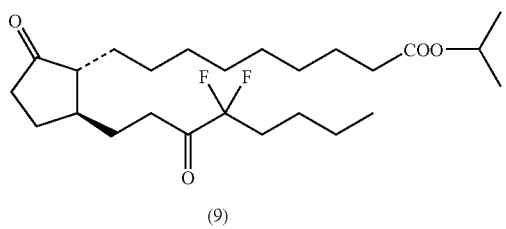
(9)

Figure 5:
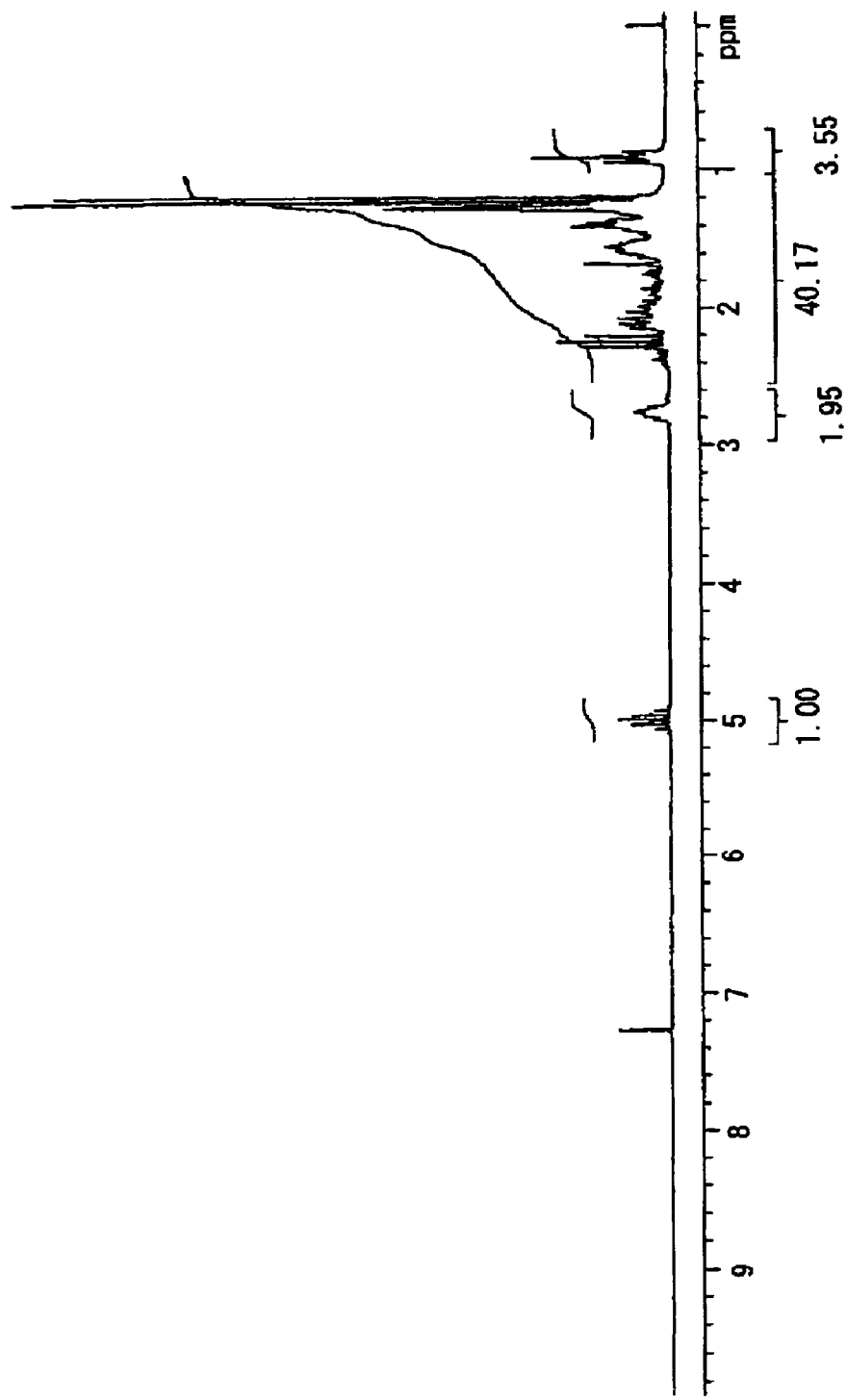
FIG. 5 is a $^1$H-NMR (200 MHz, CDCl$_3$) chart of the compound (9) obtained in Synthesis Example 3 below.
Figure 6:
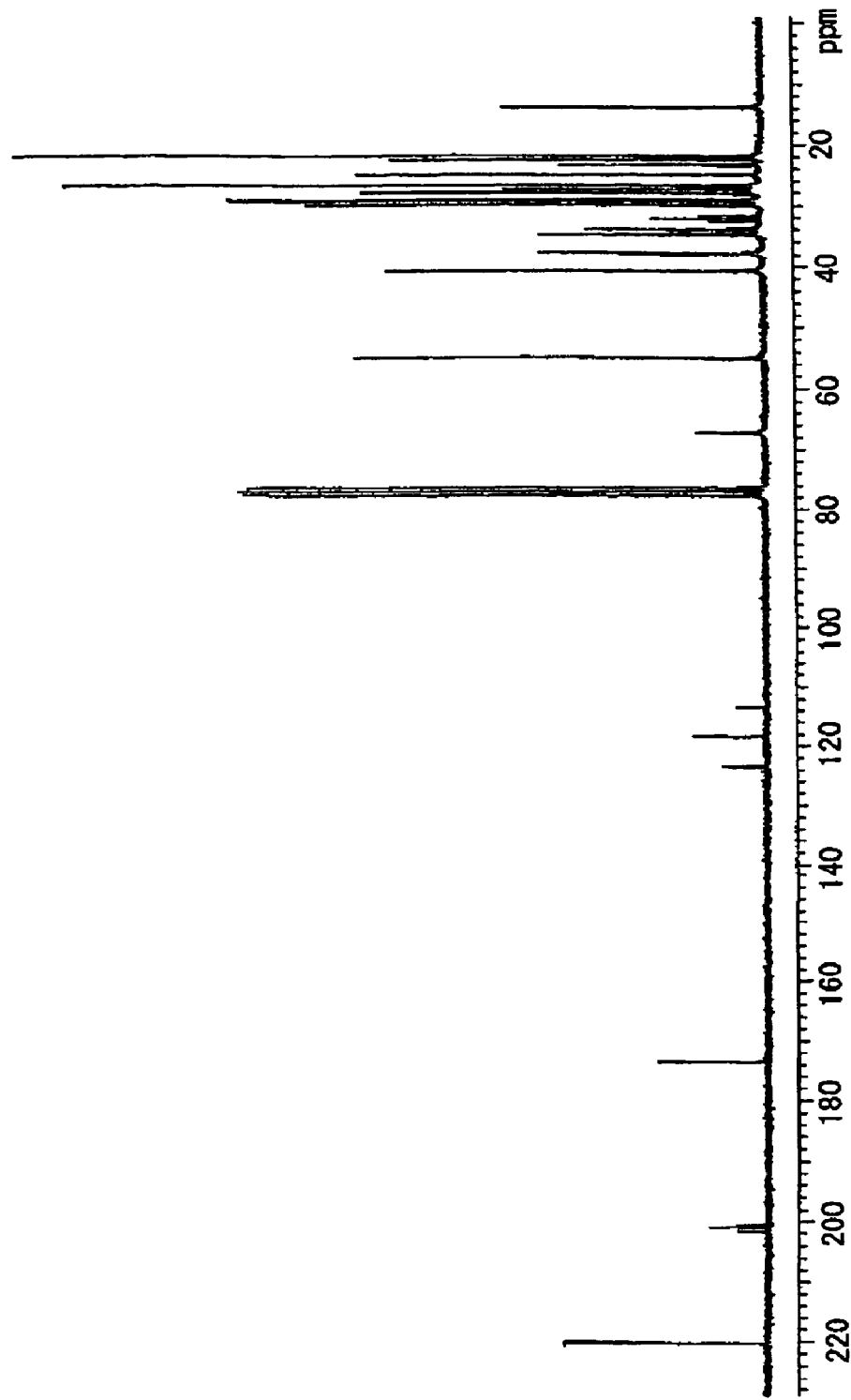
FIG. 6 is a $^{13}$C-NMR (50 MHz, CDCl$_3$) chart of the compound (9) obtained in Synthesis Example 3 below.

According to the similar manner described in Synthesis Example 1, 2-decarboxy-2-(2-carboxyethyl)-11-deoxy-13,14-dihydro-15-keto-16,16-difluoro-PGE$_1$ isopropyl ester (Compound (9)) was obtained as colorless oil. Yield: 0.402 g (1$^{st}$ step: 94.9%, 2$^{nd}$ step: 92.2%, HPLC purification: recovery 83.1%). $^1$H-NMR (200 MHz, CDCl$_3$) and $^{13}$C-NMR (50 MHz, CDCl$_3$) of the Compound (9) are shown in FIGS. 5 and 6 respectively.

Synthesis Example 4

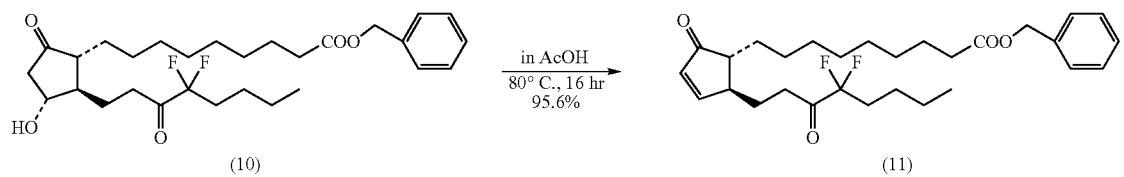

(10) → (11)

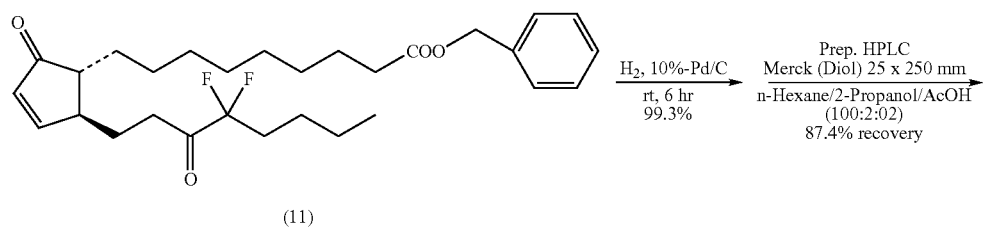

(11) →

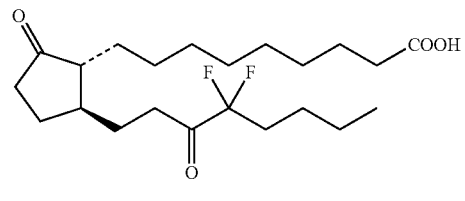

(12)

According to the similar manner described in Synthesis Example 1, 2-decarboxy-2-(2-carboxyethyl)-11-deoxy-13,14-dihydro-15-keto-16,16-difluoro-PGE$_1$ (Compound (12)) was obtained as colorless oil. Yield: 0.696 g (1$^{st}$ step: 95.6%, 2$^{nd}$ step: 99.3%, HPLC purification: recovery: 87.4%).

Figure 7:
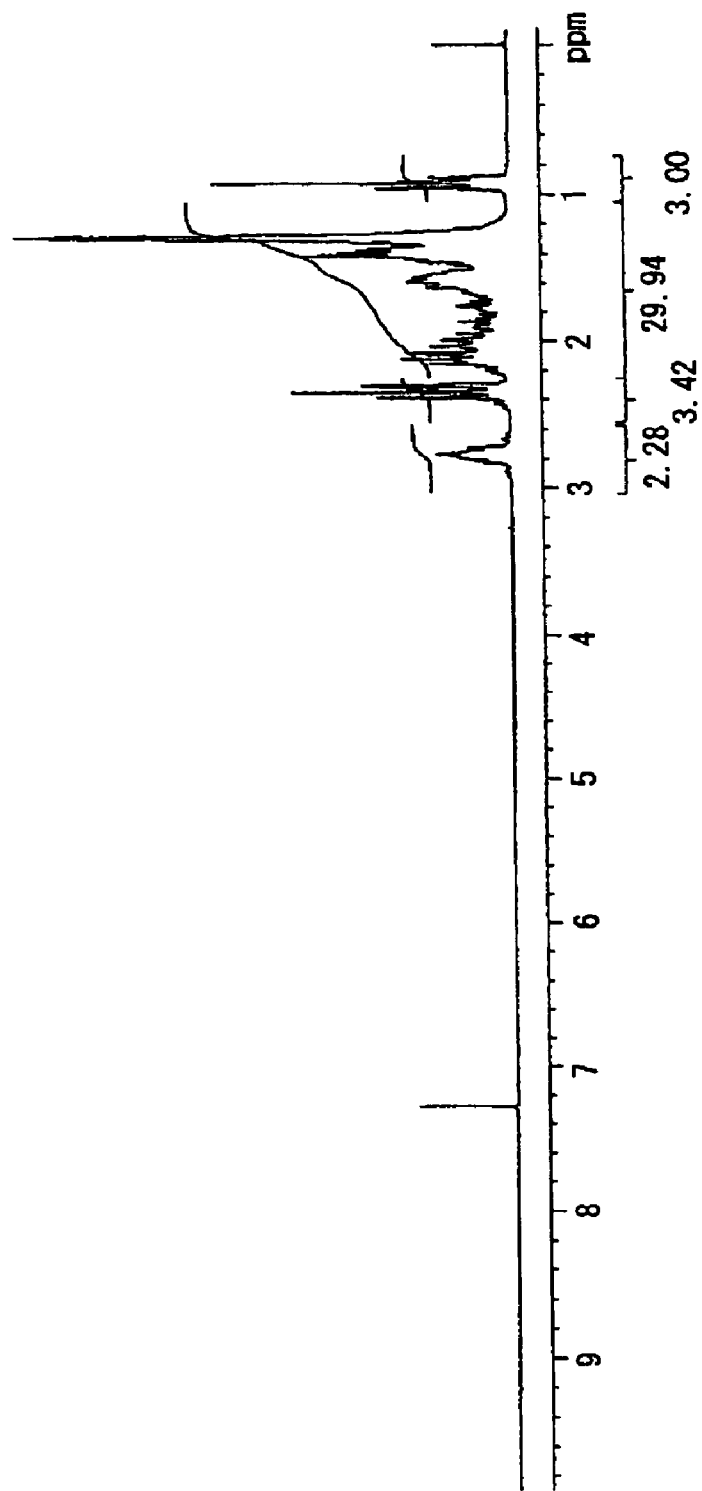
FIG. 7 is a $^1$H-NMR (200 MHz, CDCl$_3$) chart of the compound (12) obtained in Synthesis Example 4 below.
Figure 8:
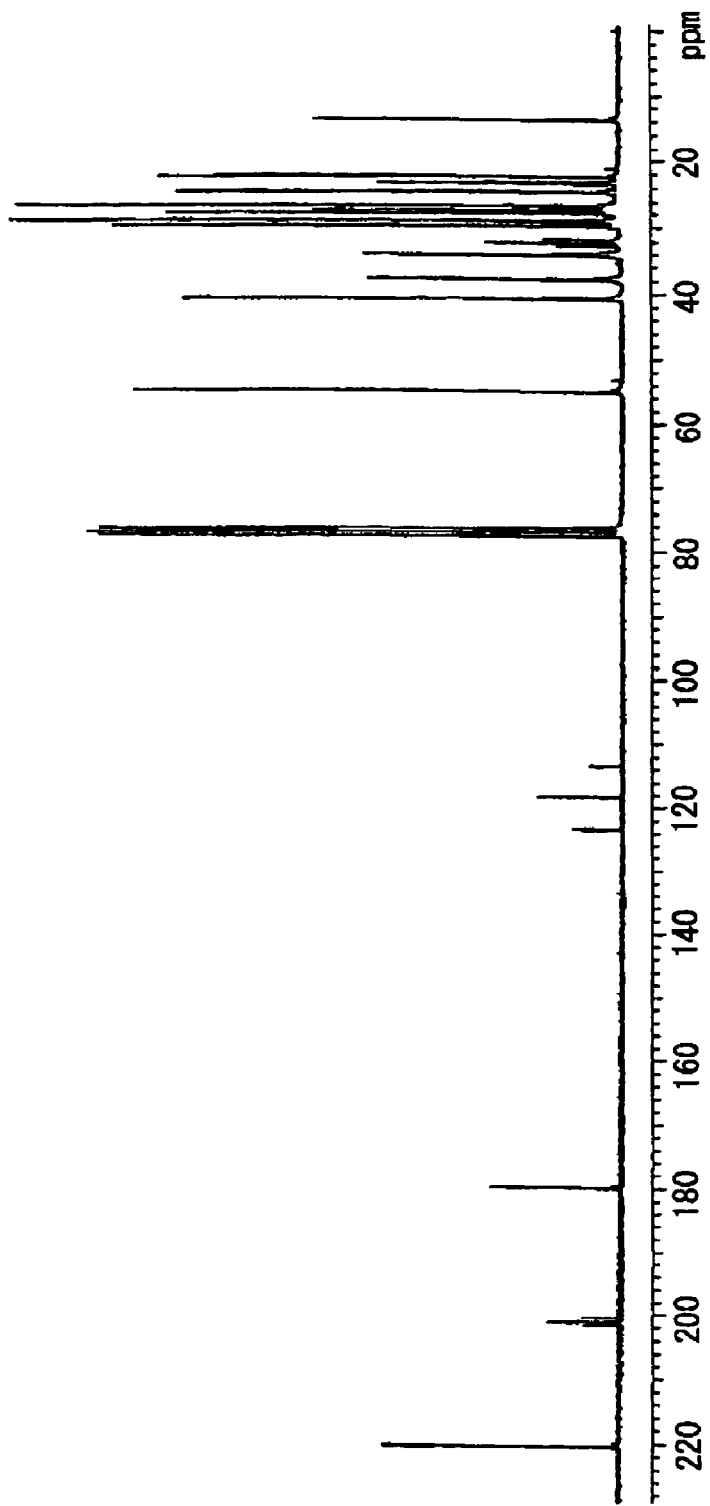
FIG. 8 is a $^{13}$C-NMR (50 MHz, CDCl$_3$) chart of the compound (12) obtained in Synthesis Example 4 below.

$^1$H-NMR (200 MHz, CDCl$_3$) and $^{13}$C-NMR (50 MHz, CDCl$_3$) of the Compound (12) are shown in FIGS. 7 and 8 respectively.

Synthesis Example 5

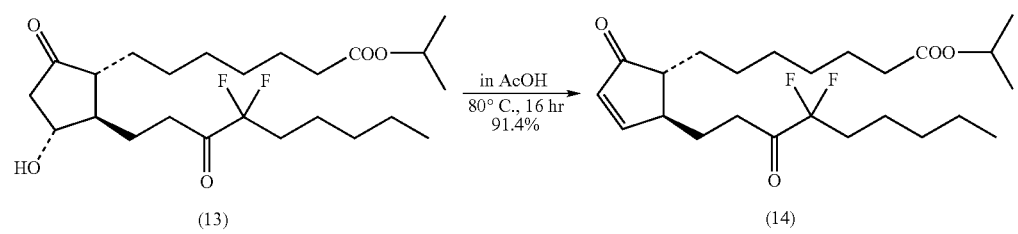

(13) → (14)

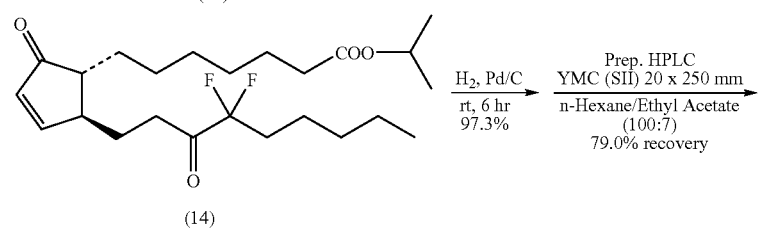

(14) →

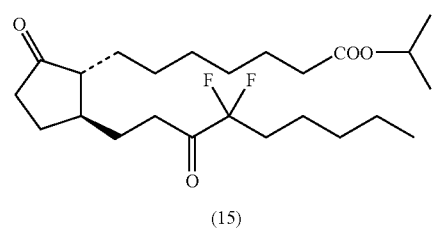

(15)

Figure 9:
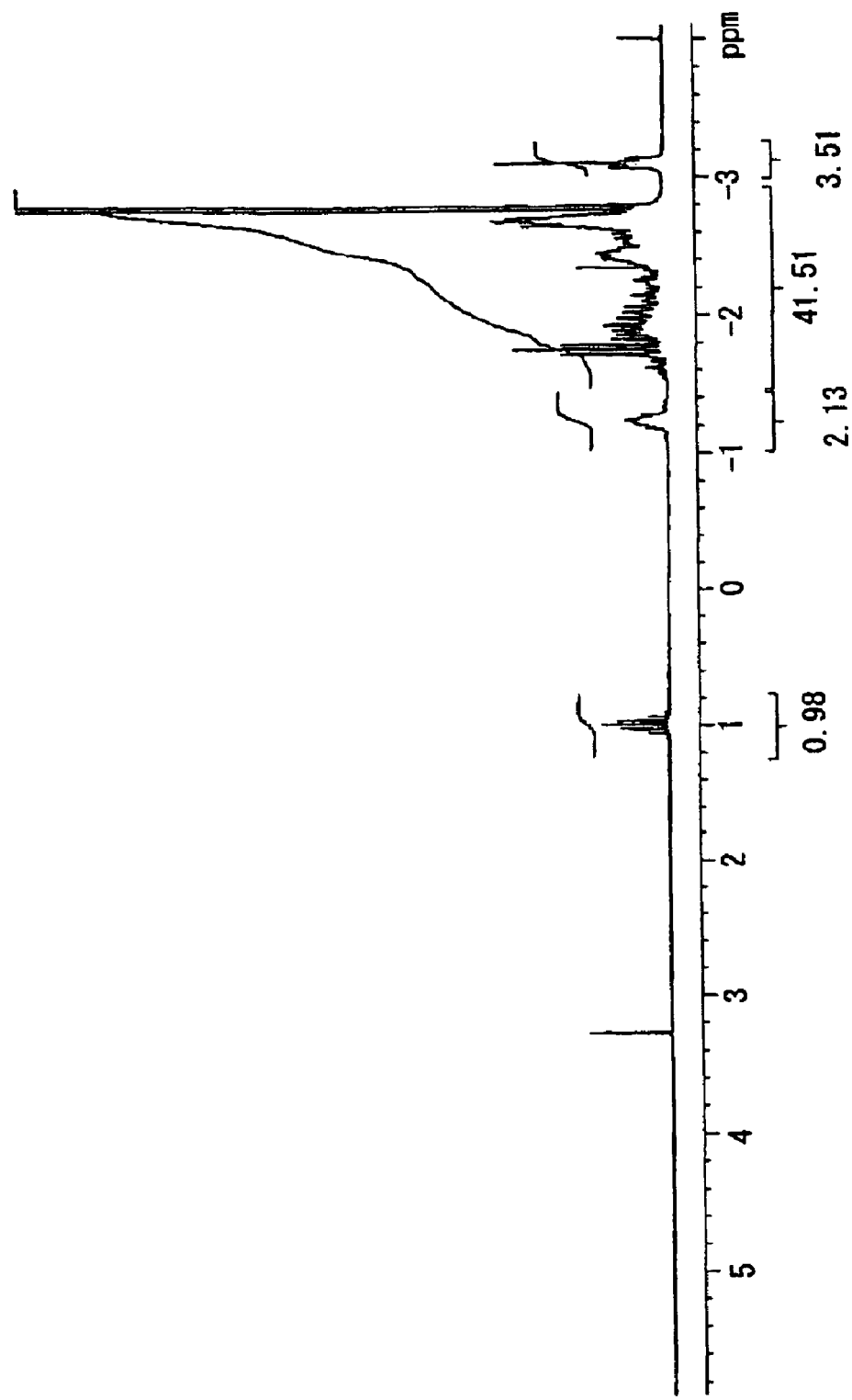
FIG. 9 is a $^1$H-NMR (200 MHz, CDCl$_3$) chart of the compound (15) obtained in Synthesis Example 5 below.
Figure 10:
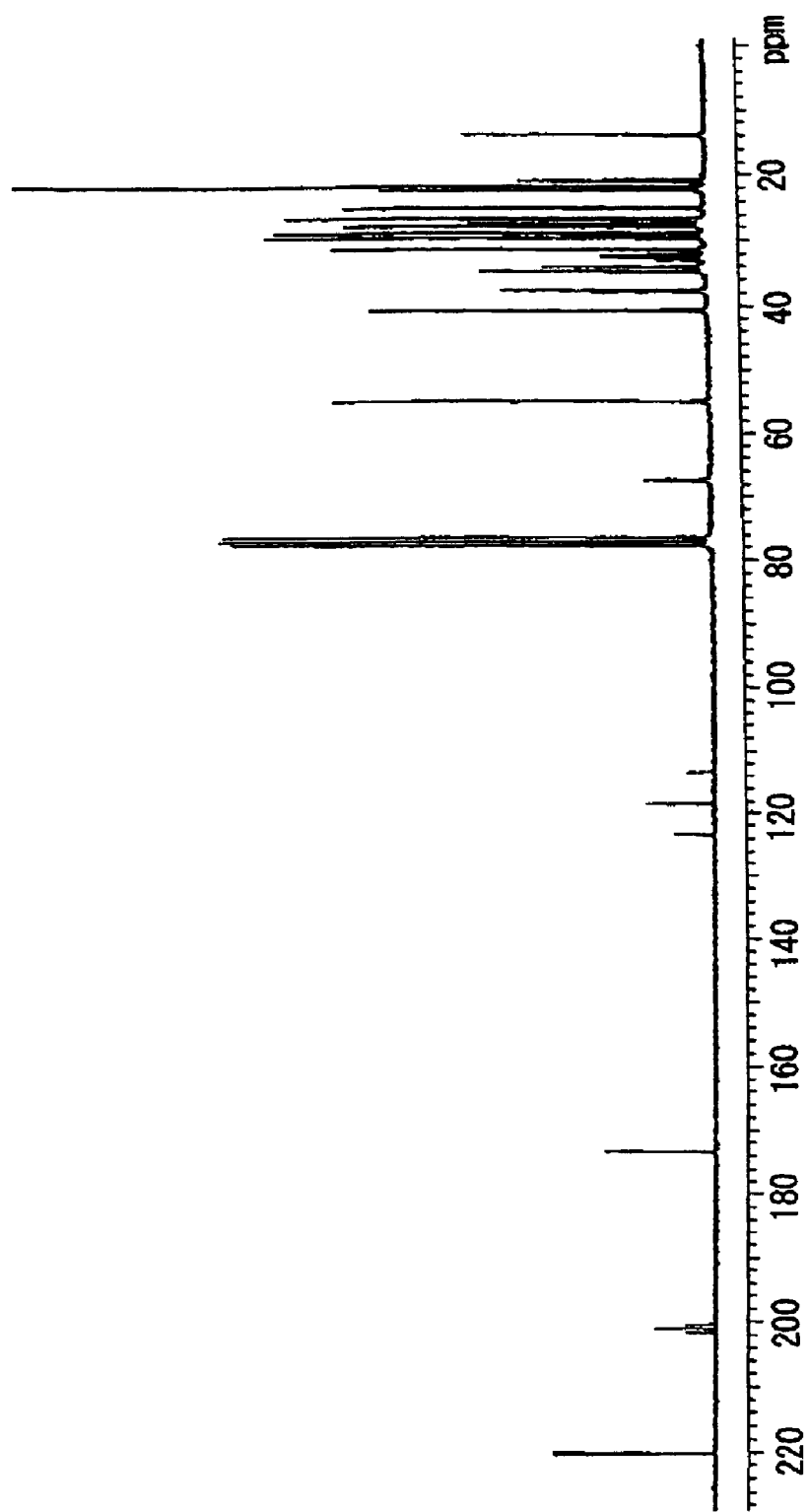
FIG. 10 is a $^{13}$C-NMR (50 MHz, CDCl$_3$) chart of the compound (15) obtained in Synthesis Example 5 below.

According to the similar manner described in Synthesis Example 1, 11-deoxy-13,14-dihydro-15-keto-16,16-difluoro-20-methyl-PGE$_1$ isopropyl ester (Compound (15)) was obtained as colorless oil. Yield: 0.271 g (1$^{st}$ step: 91.4%, 2$^{nd}$ step: 97.3%, HPLC purification: recovery: 79.0%). $^1$H-NMR (200 MHz, CDCl$_3$) and $^{13}$C-NMR (50 MHz, CDCl$_3$) of the Compound (15) are shown in FIGS. 9 and 10 respectively.

Synthesis Example 6

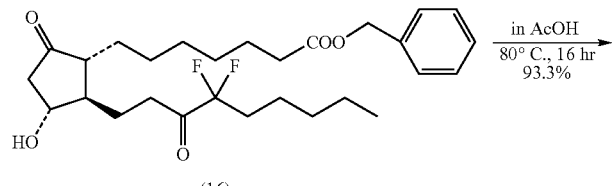
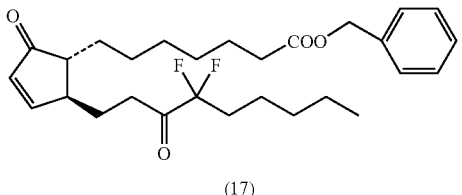
(16) → (17)

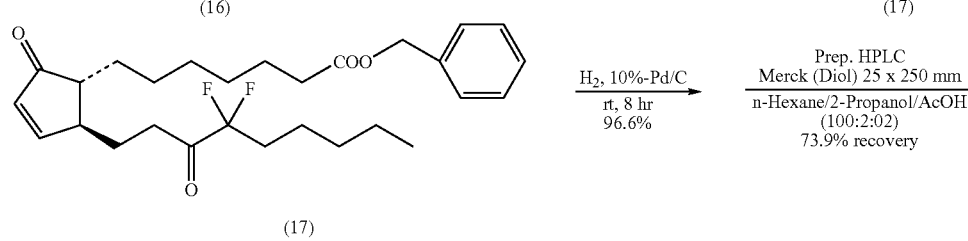
(17) →

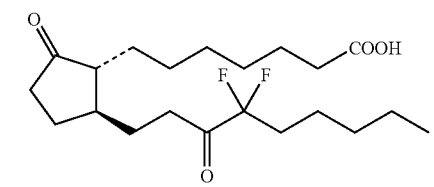

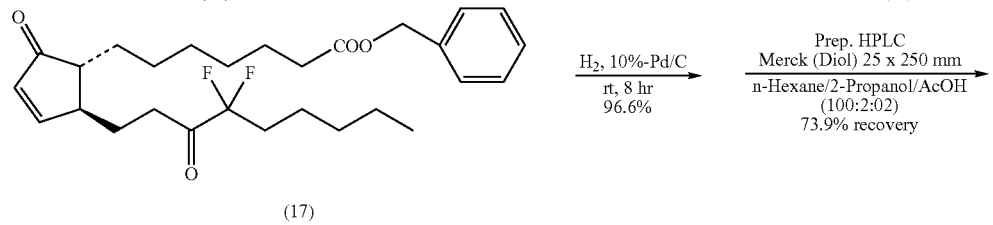
(18)

Figure 11:
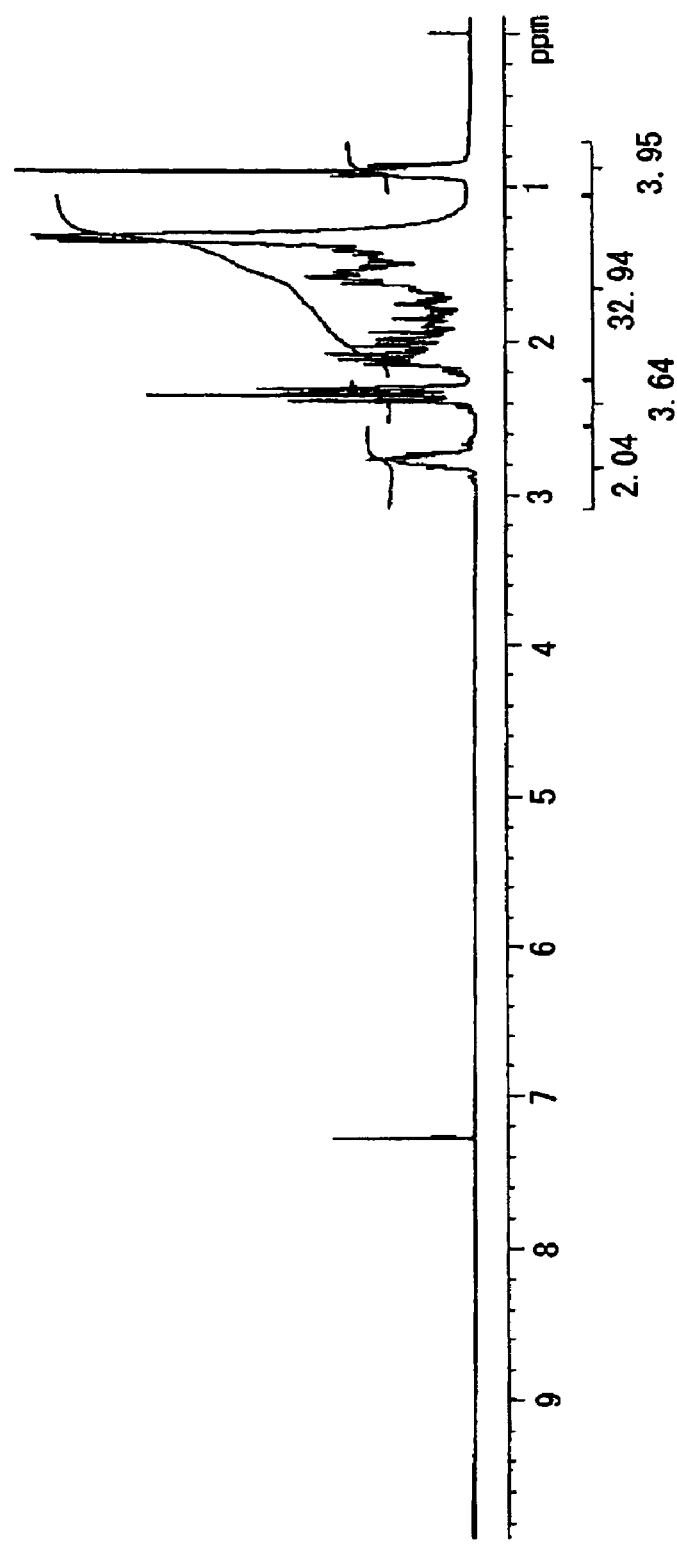
FIG. 11 is a $^1$H-NMR (200 MHz, CDCl$_3$) chart of the compound (18) obtained in Synthesis Example 6 below.
Figure 12:
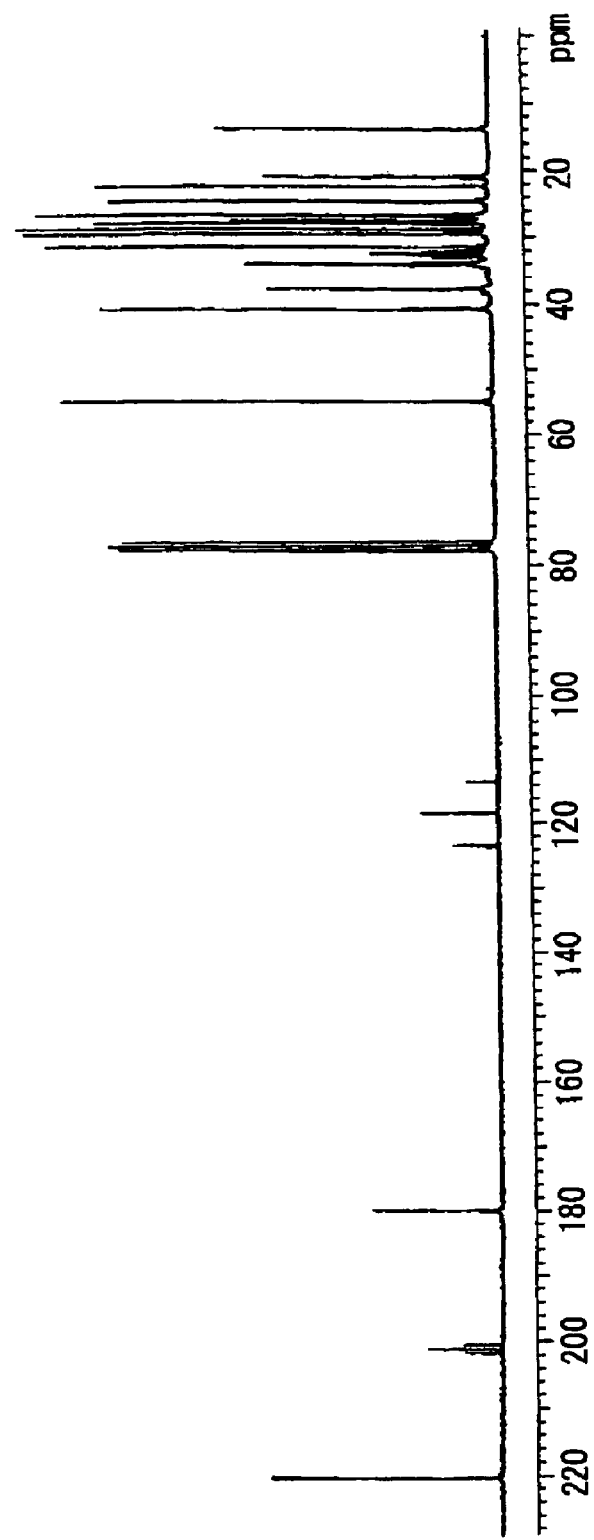
FIG. 12 is a $^{13}$C-NMR (50 MHz, CDCl$_3$) chart of the compound (18) obtained in Synthesis Example 6 below.

According to the similar manner described in Synthesis Example 1, 11-deoxy-13,14-dihydro-15-keto-16,16-difluoro-20-methyl-PGE$_1$ (Compound (18)) was obtained as colorless oil. Yield: 0.637 g (1$^{st}$ step: 93.3%, 2$^{nd}$ step: 96.6%, HPLC purification: recovery: 73.9%). $^1$H-NMR (200 MHz, CDCl$_3$) and $^{13}$C-NMR (50 MHz, CDCl$_3$) of the Compound (18) are shown in FIGS. 11 and 12 respectively.

Synthesis Example 7

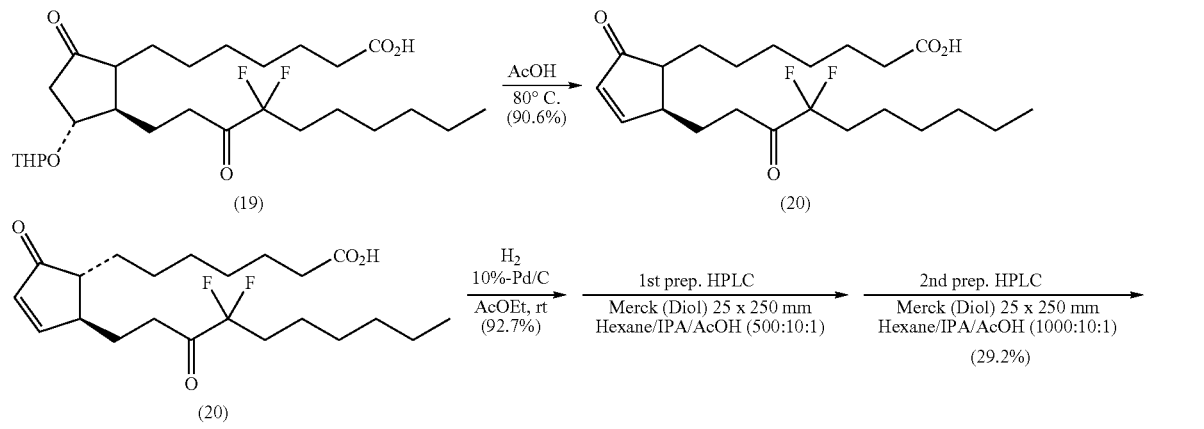

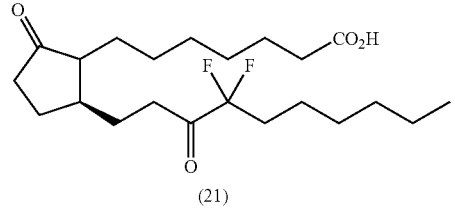

(21)

Figure 13:
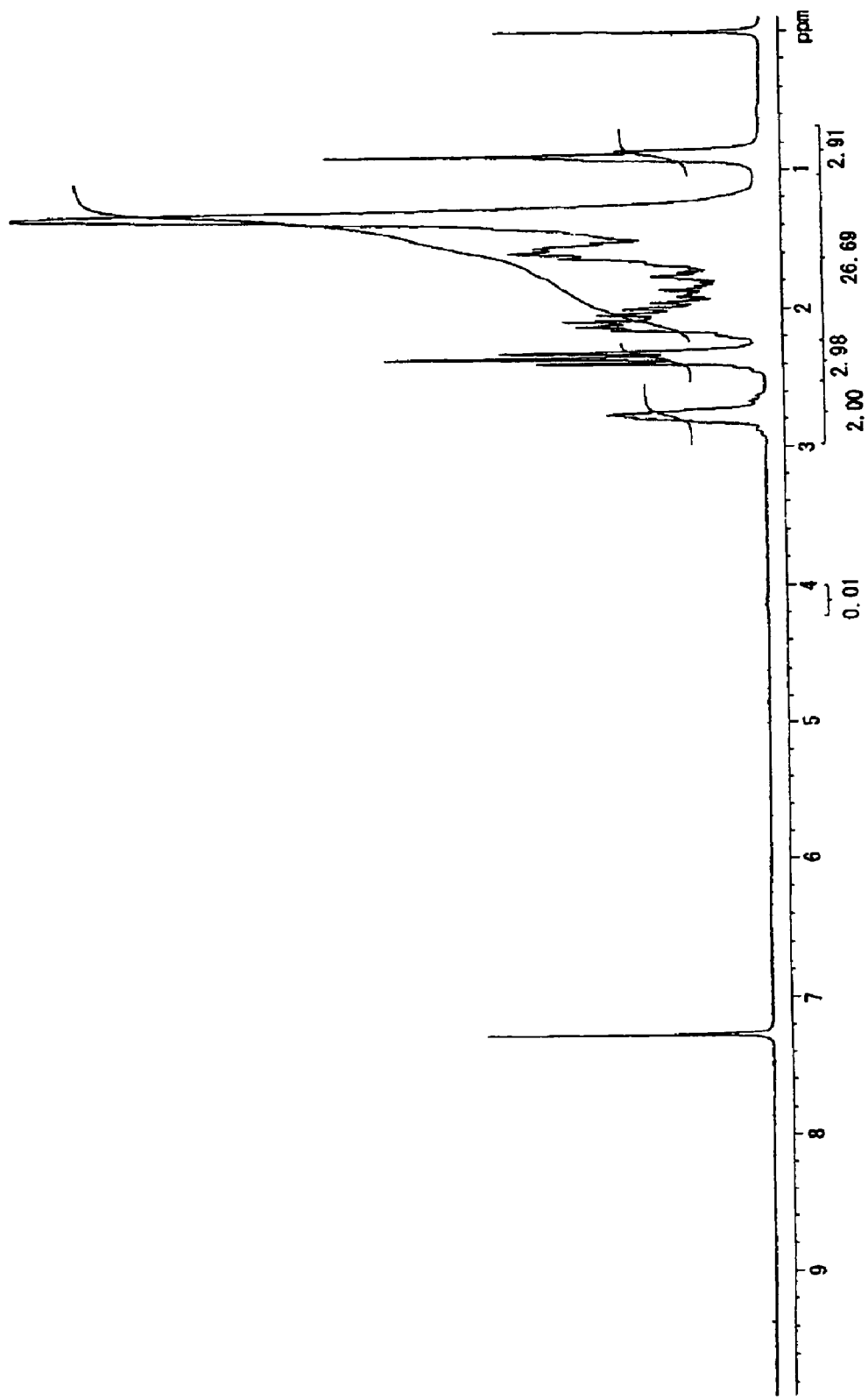
FIG. 13 is a $^1$H-NMR (200 MHz, CDCl$_3$) chart of the compound (21) obtained in Synthesis Example 7 below.
Figure 14:
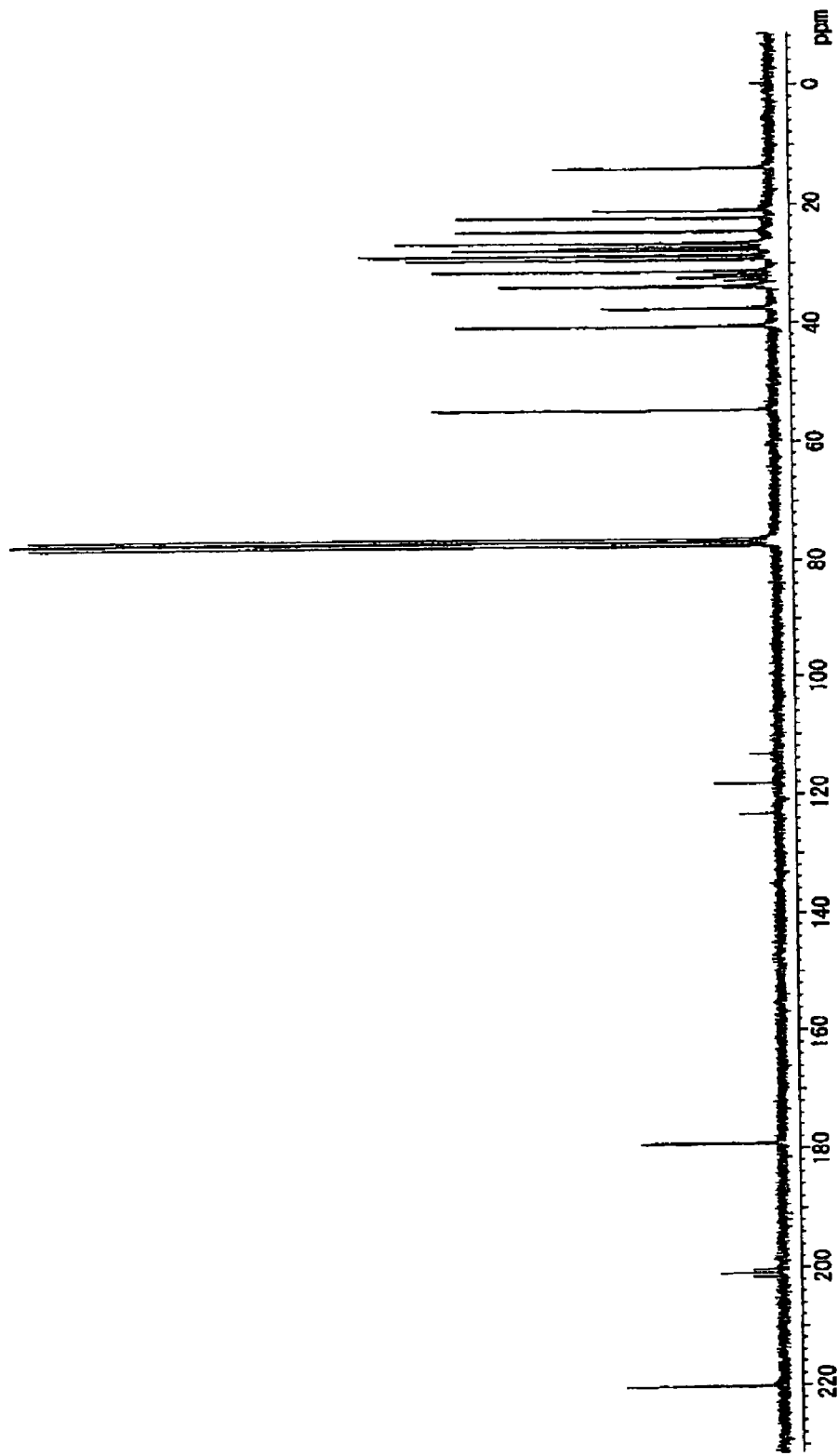
FIG. 14 is a $^{13}$C-NMR (50 MHz, CDCl$_3$) chart of the compound (21) obtained in Synthesis Example 7 below.

According to the similar manner described in Synthesis Example 1, 11-deoxy-13,14-dihydro-15-keto-16,16-difluoro-20-ethyl-PGE$_1$ (Compound (21)) was obtained as colorless oil. Yield: 0.401 g (1$^{st}$ step: 90.6%, 2$^{nd}$ step: 92.7%, HPLC purification: recovery: 29.2%). $^1$H-NMR (200 MHz, CDCl$_3$) and $^{13}$C-NMR (50 MHz, CDCl$_3$) of the Compound (21) are shown in FIGS. 13 and 14 respectively.

Synthesis Example 8

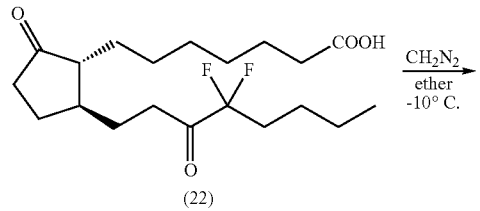

(22)

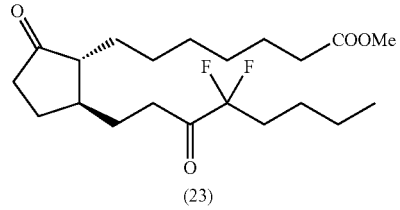

(23)

Figure 15:
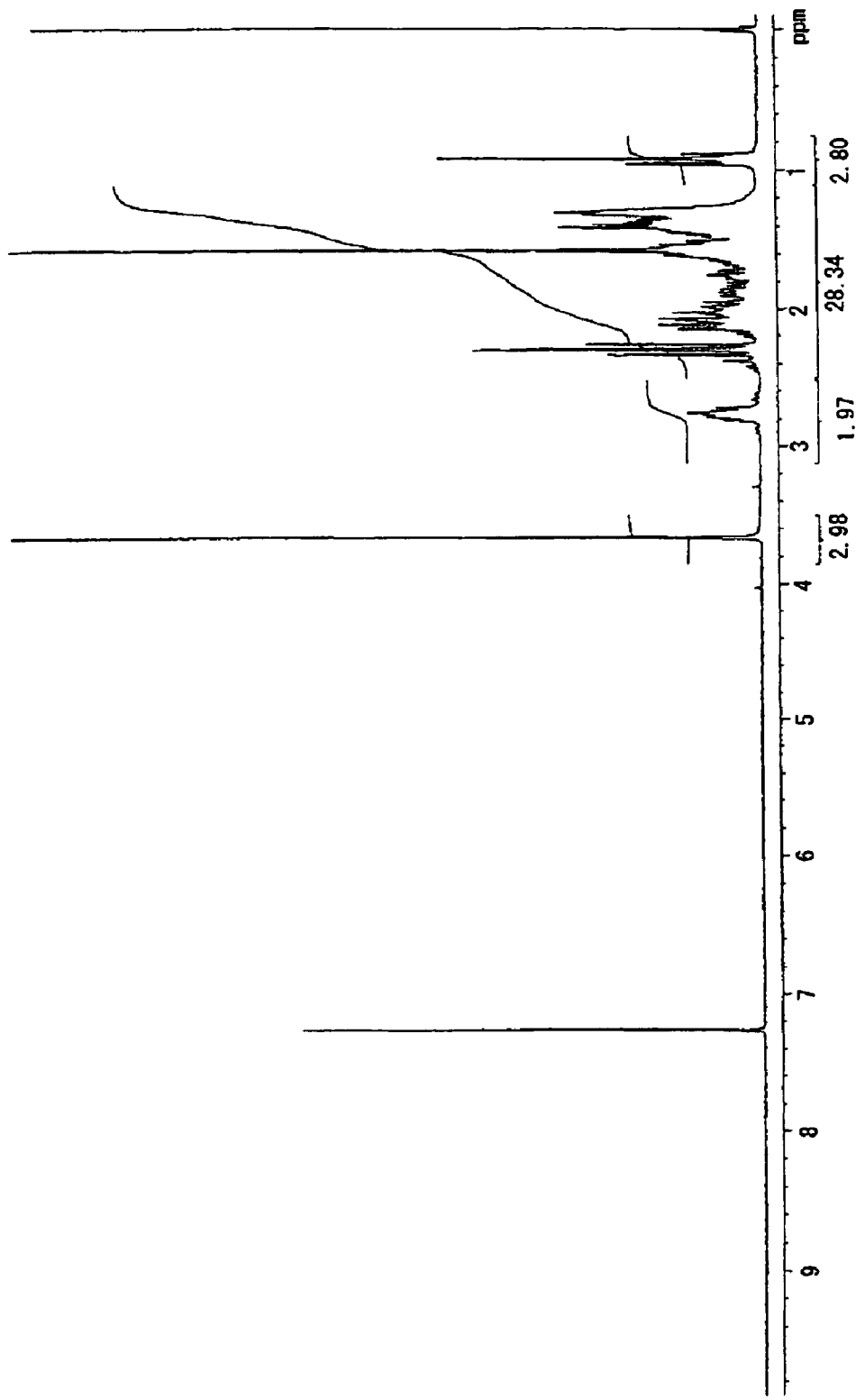
FIG. 15 is a $^1$H-NMR (200 MHz, CDCl$_3$) chart of the compound (23) obtained in Synthesis Example 8 below.
Figure 16:
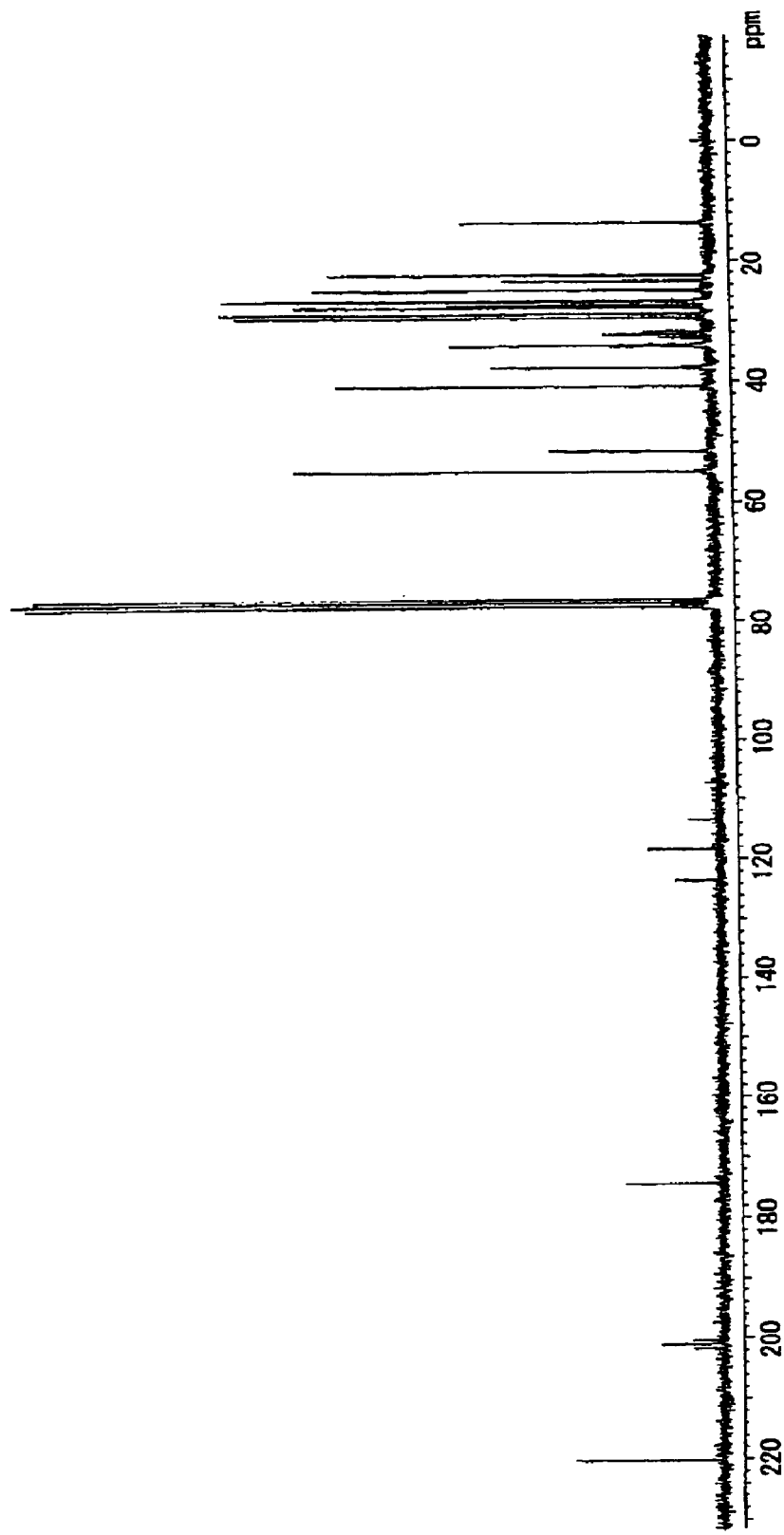
FIG. 16 is a $^{13}$C-NMR (50 MHz, CDCl$_3$) chart of the compound (23) obtained in Synthesis Example 8 below.

11-deoxy-13,14-dihydro-15-keto-16,16-difluoro-PGE$_1$ methyl ester (Compound (23)) was obtained as colorless oil by esterification of compound (22) with diazomethane. Yield: 0.860 g (72.9%, after purification by silica gel column chromatography). $^1$H-NMR (200 MHz, CDCl$_3$) and $^{13}$C-NMR (50 MHz, CDCl$_3$) of the Compound (23) were shown in FIGS. 15 and 16.

Synthesis Example 9

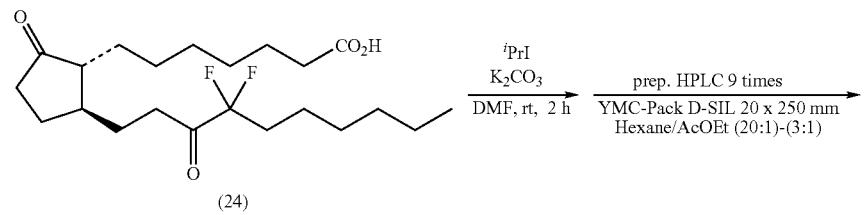

(24)

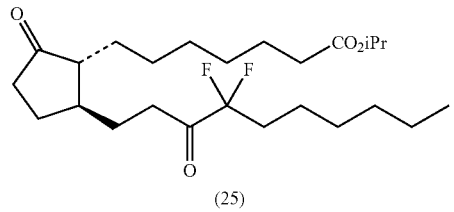

(25)

Figure 17:
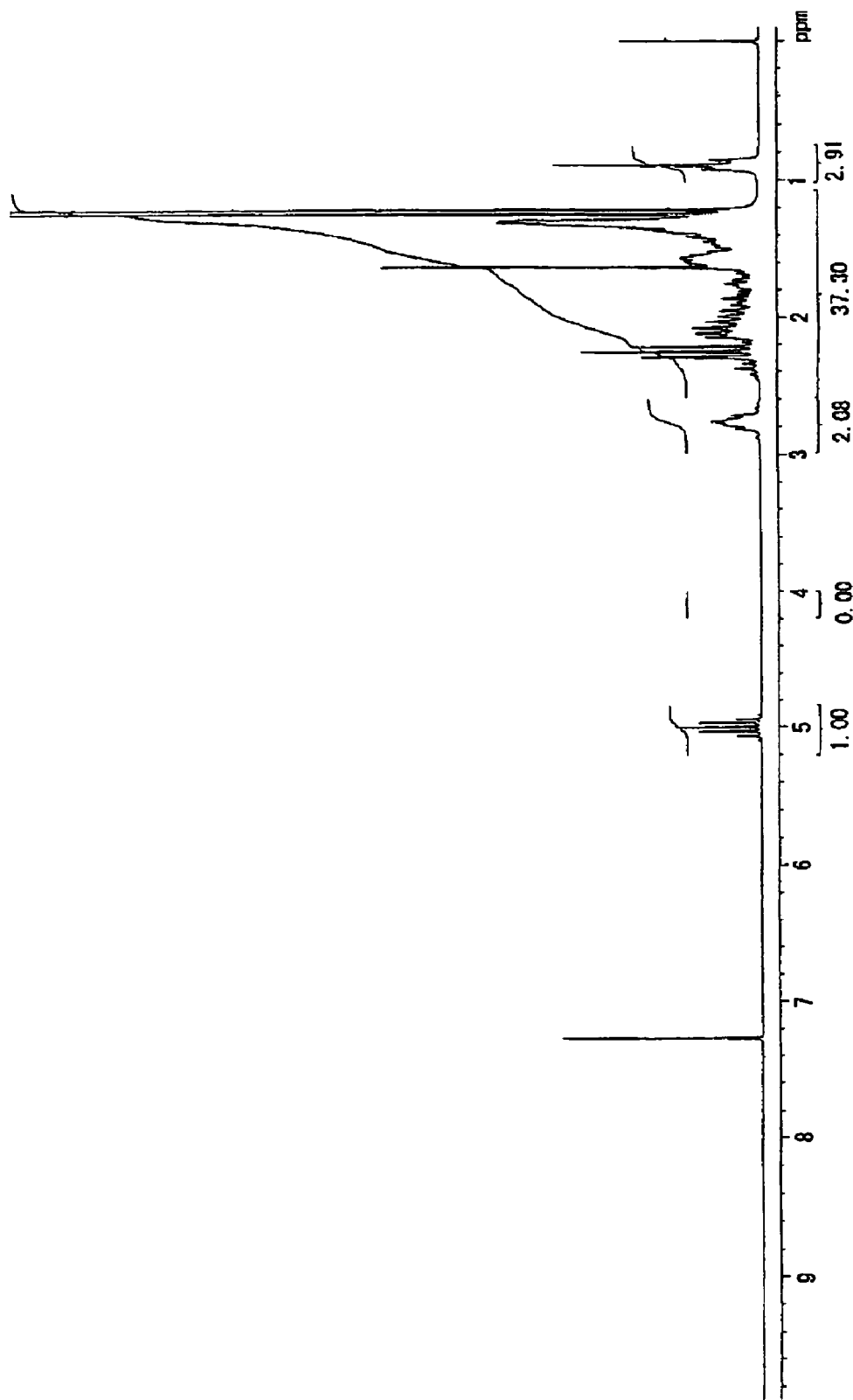
FIG. 17 is a $^1$H-NMR (200 MHz, CDCl$_3$) chart of the compound (25) obtained in Synthesis Example 9 below.
Figure 18:
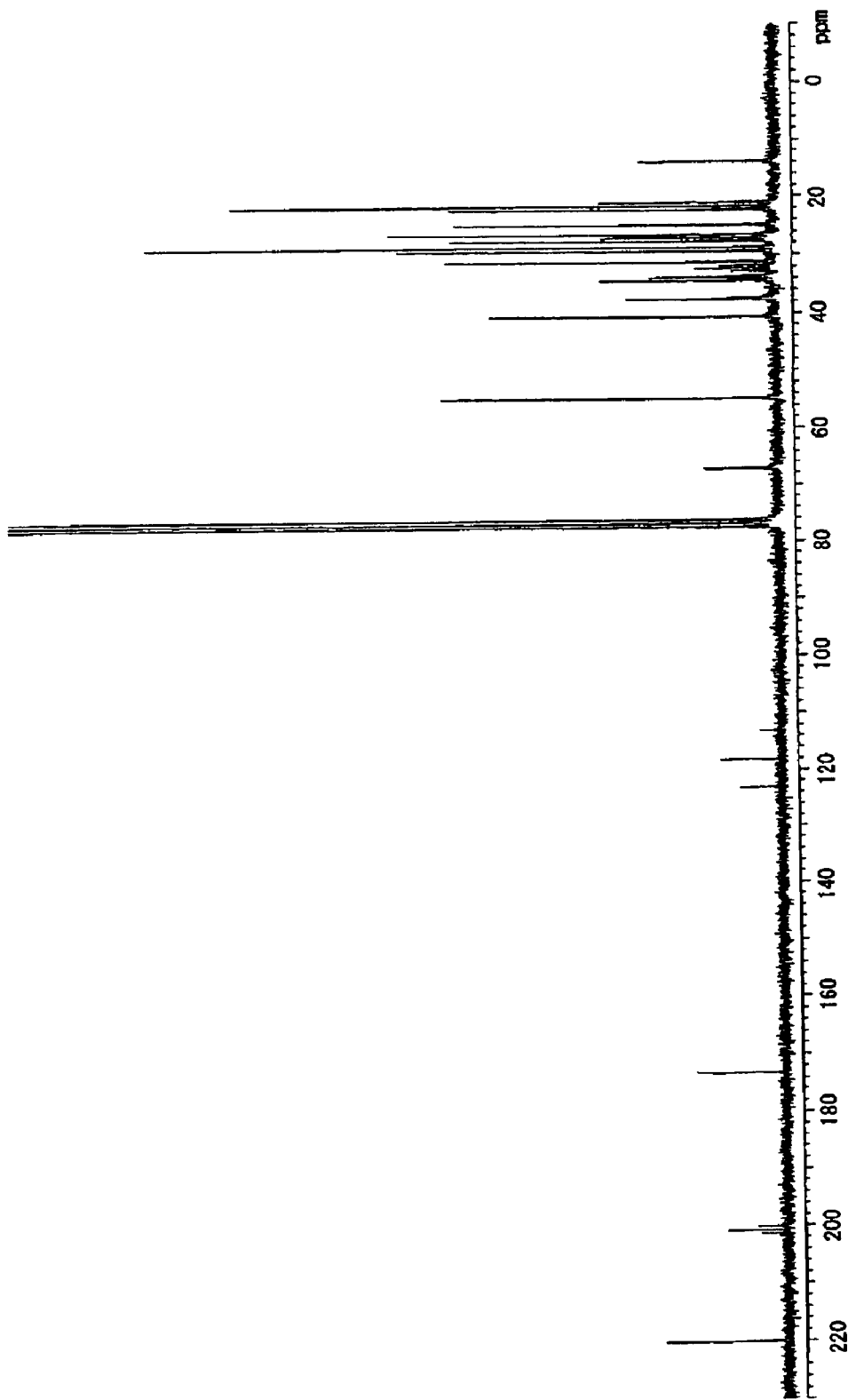
FIG. 18 is a $^{13}$C-NMR (50 MHz, CDCl$_3$) chart of the compound (25) obtained in Synthesis Example 9 below.

Compound (24) (0.67 g, 1.66 mmol) was dissolved in DMF (13 mL), and added K$_2$CO$_3$ (460.1 mg, 3.33 mmol) and isopropyl iodide (831 μL, 8.32 mmol). The solution was stirred at room temperature for 2 hours. The reaction mixture was cooled with ice, added water (10 mL) and brine, and extracted with ethyl acetate (30 mL). The organic layer was washed with brine (10 mL), dried with anhydrous magnesium sulfate, and then concentrated under reduced pressure. The residue was purified by silica gel column chromatography (silica gel FL60D (50 g), Fuji Silysia, hexane/ethyl acetate (5:1)) to obtain crude 11-deoxy-13,14-dihydro-15-keto-16,16-difluoro-20-ethyl-PGE$_1$ isopropyl ester (compound (25)) (0.70 g, 94.6%). The crude compound (25) was purified by preparative HPLC to obtain compound (25) as colorless oil. Yield 245.8 mg (35.1%). $^1$H-NMR (200 MHz, CDCl$_3$) and $^{13}$C-NMR (50 MHz, CDCl$_3$) for the Compound (25) are shown in FIGS. 17 and 18 respectively.

Synthesis Example 10

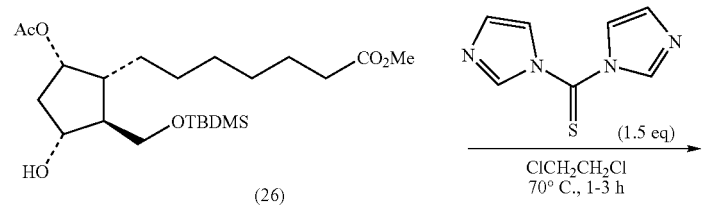

(26)

-continued
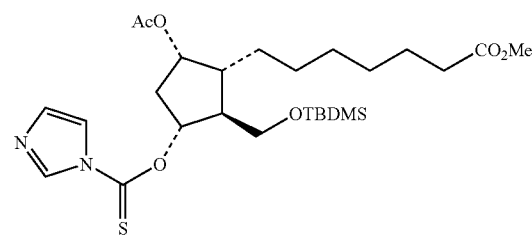
(27)
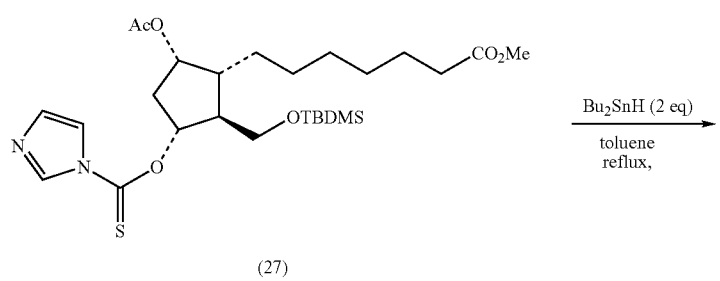
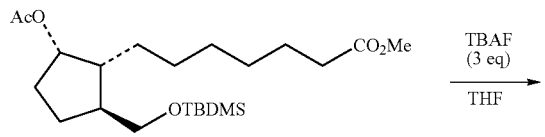
(28)
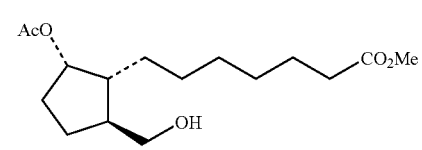
(29)
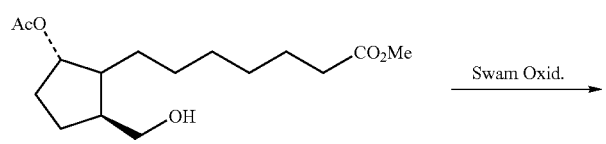
(29)
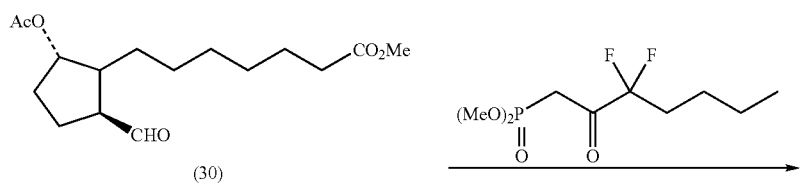
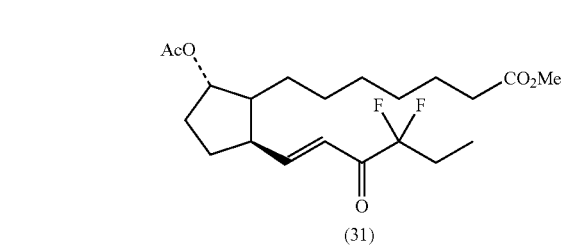
(31)

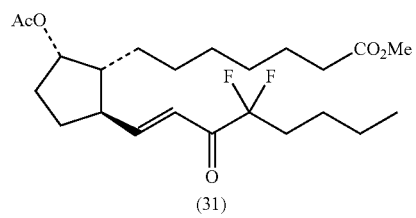

(31)

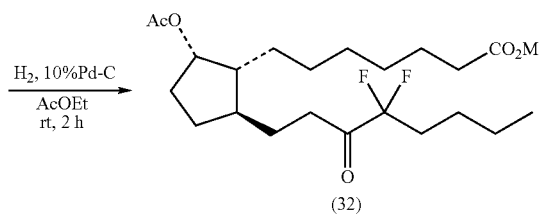

(32)

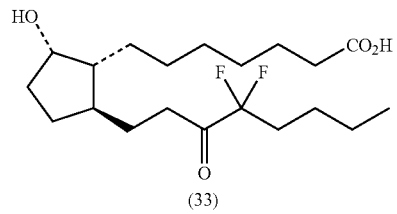

(33)

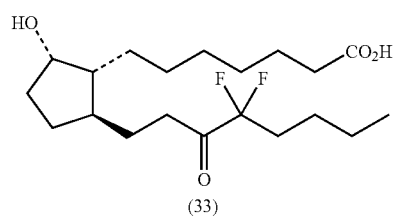

(33)

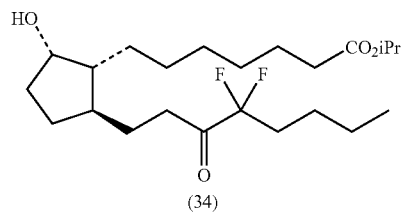

(34)

Compound (26) (8.71 g, 20.2 mmol) was dissolved in 1,2-dichloroethane (70 mL) and added 1,1'-Thiocarbonyldiimidazole (5.41 g, 30.3 mmol). The solution was stirred at 70° C. for an hour. The reaction mixture was cooled to room temperature, and then concentrated under reduced pressure. The residue was purified by silica gel column chromatography (silica gel BW-300SP (650 g), Fuji Silysia, hexane/ethyl acetate (1:1)) to obtain compound (27) as light yellow oil (10.61 g, 97.0%).

Bu$_3$SnH (11.21 g, 38.5 mmol) was dissolved in toluene (224 mL), and refluxed by heating. The solution of Compound (27) (10.41 g, 19.2 mmol) in toluene (208 mL) was dropped to the reaction mixture at a reflux temperature for 70 minutes. And then, the reaction mixture was cooled to room temperature, concentrated under reduced pressure to obtain crude compound (28) as light yellow oil.

The crude compound (28) (19.2 mmol) was dissolved in THF (52 mL) and TBAF solution (1.0 M in THF, 38.5 mL, 38.5 mmol) was dropped for 10 minutes. After an hour, TBAF solution (1.0 M in THF, 19.2 mL, 19.2 mmol) was dropped to the solution. After stirring for total 3.5 hours, the reaction mixture was concentrated under reduced pressure. The residue was purified by silica gel column chromatography (silica gel BW-300SP (1,000 g), Fuji Silysia, hexane/ethyl acetate (1:1)) to obtain compound (29) as yellow oil (4.01 g, 69.3%).

Compound (31) was obtained from compound (29) by Swern oxidation and introduction of ω-chain.

Compound (31) (807.4 mg, 1.88 mmol) was hydrogenated in ethyl acetate (8 mL) under the presence of 10% palladium-carbon at room temperature for 2 hours. The reaction mixture was filtered through a Celite pad, and the filtrate was concentrated under reduced pressure to obtain crude compound (32) as the light brown oil.

The crude compound (32) (1.88 mmol) was dissolved in EtOH (8 mL). 1N—NaOH solution (7.4 mL, 7.4 mol) was dropped to the solution at room temperature for 10 minutes. The reaction mixture was stirred at room temperature for 10 hours, and then cooled with ice. 1N—HCl (7.1 mL) was dropped to the reaction mixture to adjust pH around 3-4. Then the reaction mixture was extracted with TBME (30 mL). The organic layer was washed with water (10 mL) and brine (10 mL), dried with anhydrous magnesium sulfate, and then concentrated under reduced pressure. The residue was purified by silica gel column chromatography (silica gel 15% water including FL-60D (80 g), Fuji Silysia, hexane/ethyl acetate (2:1)) to obtain compound (33) as light yellow oil (481.4 mg, 68.8%).

Figure 19:
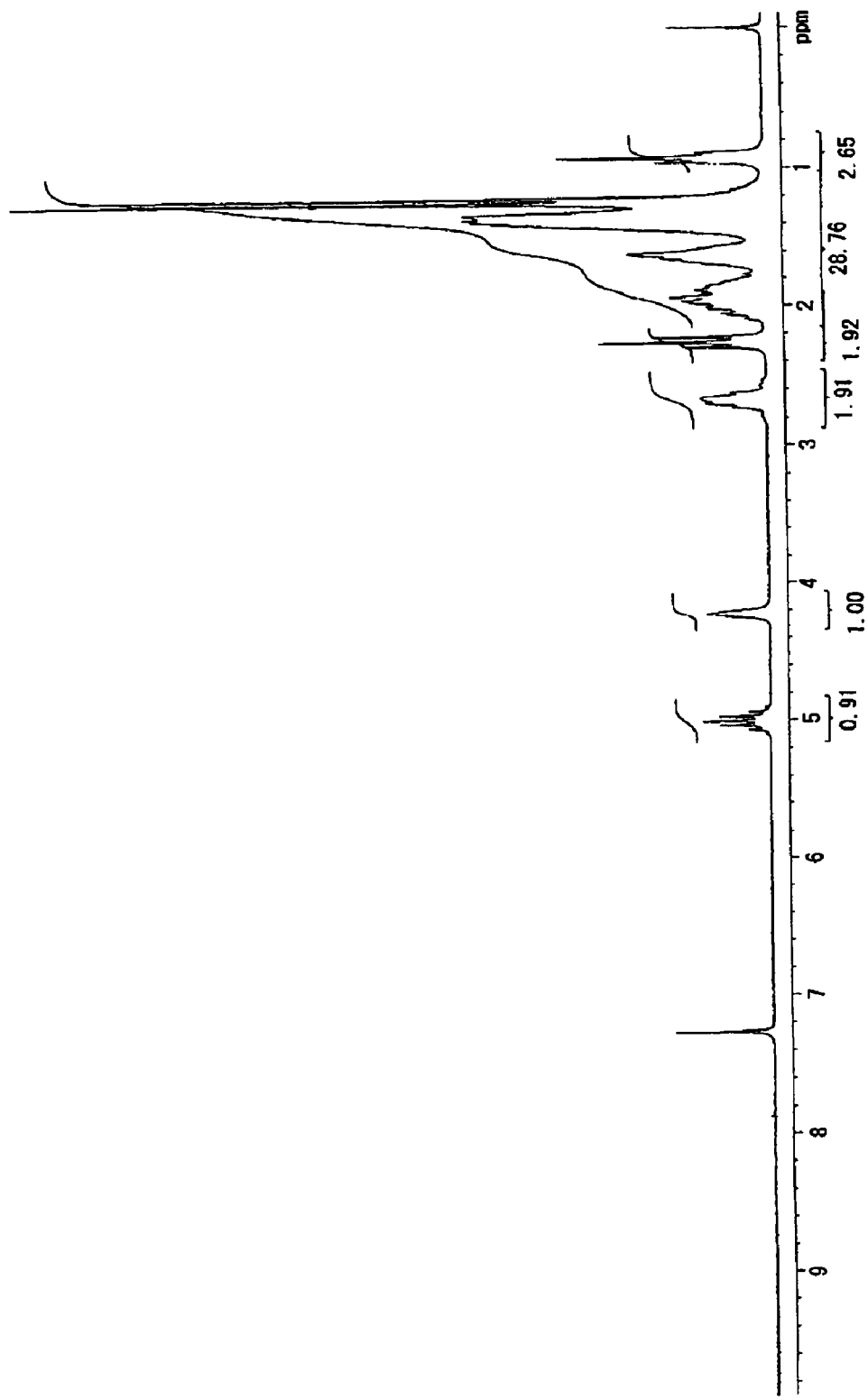
FIG. 19 is a $^1$H-NMR (200 MHz, CDCl$_3$) chart of the compound (34) obtained in Synthesis Example 10 below.
Figure 20:
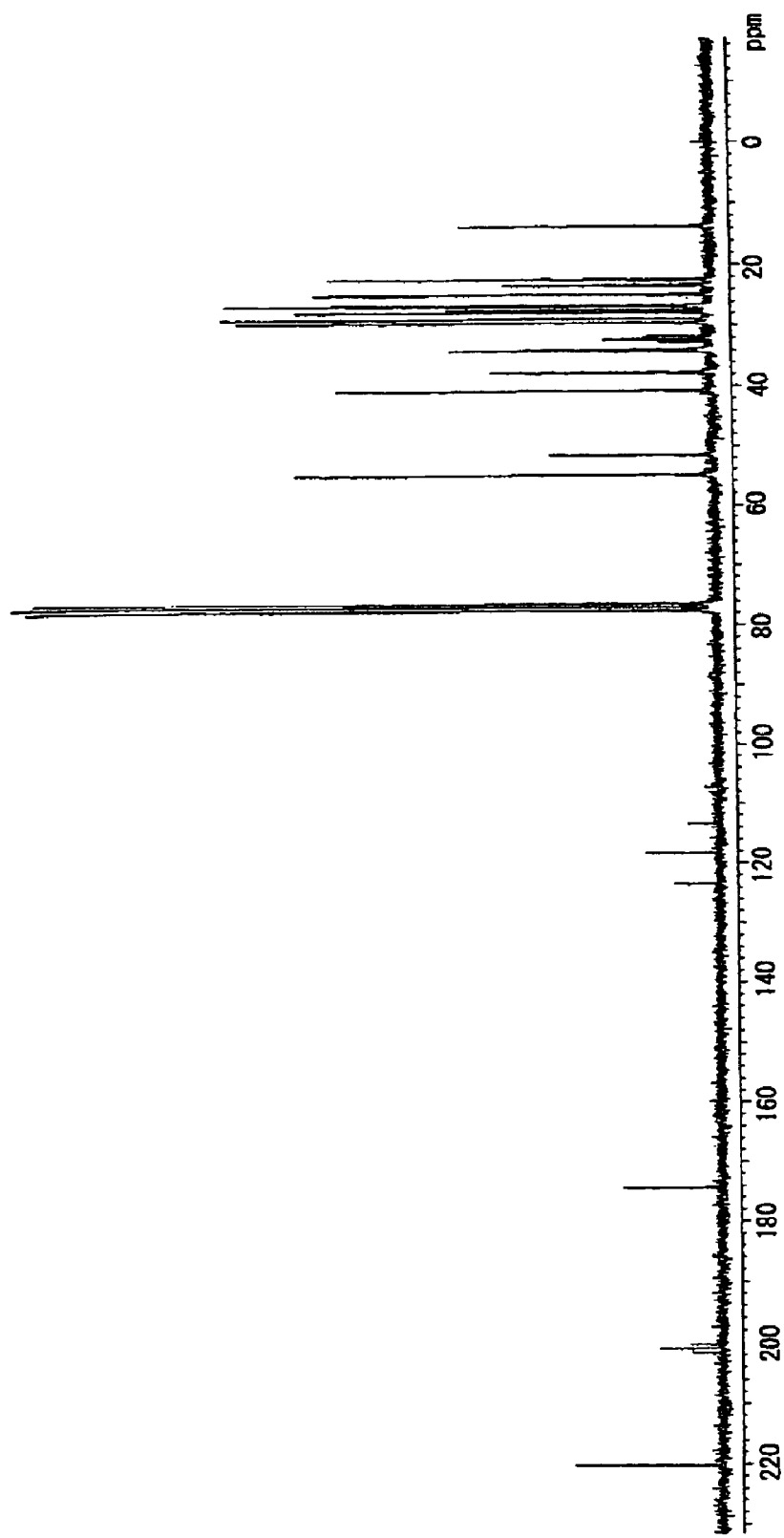
FIG. 20 is a $^{13}$C-NMR (50 MHz, CDCl$_3$) chart of the compound (34) obtained in Synthesis Example 10 below.

According to the similar manner described in Synthesis Example 9, 11-deoxy-13,14-dihydro-15-keto-16,16-difluoro-PGF$_{1\alpha}$ isopropyl ester (compound (34)) was obtained from compound (33) as colorless oil. Yield: 166.6 mg (reaction step 91.9%: HPLC purification: recovery: 55.4%). $^1$H-NMR (200 MHz, CDCl$_3$) and $^{13}$C-NMR (50 MHz, CDCl$_3$) of the Compound (34) are shown in FIGS. 19 and 20 respectively.

What is claimed is:

1. A method for treating a central nervous system disorder in a mammalian subject, which comprises administering an effective amount of an 11-deoxy-prostaglandin compound represented by the formula (III):

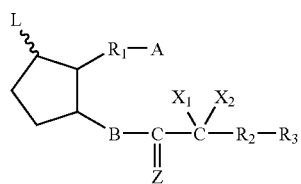
(III)

wherein L is hydrogen, hydroxy, halogen, lower alkyl, hydroxy(lower)alkyl, lower alkanoyloxy or oxo, wherein the five-membered ring may optionally have at least one double bond;

A is —CH$_3$, —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$, —CH=CH—CH$_2$—, —CH$_2$—CH=CH—, —C≡C—CH$_2$—or —CH$_2$—C≡C—;

C=Z is C=O;

X$_1$ and X$_2$ are hydrogen, lower alkyl, or halogen;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and R$_2$ is a single bond or lower alkylene; and R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one of carbon atom in the aliphatic hydrocarbon is optionally substituted by oxygen, nitrogen or sulfur; to a subject in need thereof.

2. The method as described in claim 1, wherein said 11-deoxy-prostaglandin compound is 11-deoxy-15-keto-16-mono or dihalogen-prostaglandin compound.

3. The method as described in claim 1, wherein said 11-deoxy-prostaglandin compound is 11-deoxy-13,14-dihydro-15-keto-16-mono or dihalogen-prostaglandin compound.

4. The method as described in claim 1, wherein said 11-deoxy-prostaglandin compound is 11-deoxy-13,14-dihydro-15-keto-16-mono or difluoro-prostaglandin compound.

5. The method as described in claim 1, wherein said 11-deoxy-prostaglandin compound is 11-deoxy-13,14-dihydro-15-keto-16-mono or dihalogen-prostaglandin E or F compound.

6. The method as described in claim 1, wherein said prostaglandin compound is 11-deoxy-13,14-dihydro-15-keto-16-mono or difluoro-prostaglandin E or F compound.

7. The method as described in claim 1, wherein said prostaglandin compound is 11-deoxy-13,14-dihydro-15-keto-16,16-difluoro-prostaglandin E$_1$ compound.

8. The method as described in claim 1, wherein said prostaglandin compound is 11-deoxy-13,14-dihydro-15-keto-16,16-difluoro-PGE$_1$, 11-deoxy-13,14-dihydro-16,16-difluoro-PGE$_1$, and/or 11-deoxy-13,14-dihydro-15-keto-16,16-difluoro-PGE$_1$ methyl ester.

9. The method as described in claim 1, wherein the central nervous system disorder is ischemic disease, dementia, Alzheimer's disease or cerebral infarct, and said prostaglandin compound is 11-deoxy-13,14-dihydro-15-keto-16,16-difluoro-PGE$_1$, 11-deoxy-13,14-dihydro-16,16-difluoro-PGE$_1$, and/or 11-deoxy-13,14-dihydro-15-keto-16,16-difluoro-PGE$_1$ methyl ester.

10. The method as described in claim 1, wherein the central nervous system disorder is Alzheimer's disease and said prostaglandin compound is 11-deoxy-13,14-dihydro-15-keto-16,16-difluoro-PGE$_1$.

11. The method as described in claim 1, wherein said prostaglandin compound is selected from the group consisting of:
- 11-deoxy-13,14-dihydro-15-keto-16,16-difluoro-PGE$_1$ isopropyl ester,
- 2-decarboxy-2-(2-carboxyethyl)-11-deoxy-13,14-dihydro-15-keto-16,16-difluoro-PGE$_1$ isopropyl ester,
- 2-decarboxy-2-(2-carboxyethyl)-11-deoxy-13,14-dihydro-15-keto-16,16-difluoro-PGE$_1$,
- 11-deoxy-13,14-dihydro-15-keto-16,16-difluoro-20-methyl-PGE$_1$ isopropyl ester,
- 11-deoxy-13,14-dihydro-15-keto-16,16-difluoro-20-methyl-PGE$_1$,
- 11-deoxy-13,14-dihydro-15-keto-16,16-difluoro-20-ethyl-PGE$_1$,
- 11-deoxy-13,14-dihydro-15-keto-16,16-difluoro-PGE$_1$ methyl ester,
- 11-deoxy-13,14-dihydro-15-keto-16,16-difluoro-20-ethyl-PGE$_1$ isopropyl ester, and
- 11-deoxy-13,14-dihydro-15-keto-16,16-difluoro-PGF$_{1\alpha}$ isopropyl ester.

12. The method as described in claim 1, wherein the central nervous system disorder is a cerebrovascular disorder.

13. The method as described in claim 1, wherein the central nervous system disorder is cerebrovascular disorder, neuronal disorder or ischemic disease.

14. The method as described in claim 1, wherein the central nervous system disorder is Alzheimer's disease, dementia, ischemic disease or cerebral infarct.

* * * * *